(12) United States Patent
Yang et al.

(10) Patent No.: US 9,988,410 B2
(45) Date of Patent: Jun. 5, 2018

(54) SUBSTITUTED BIS INDENYL METALLOCENE CATALYST COMPOUNDS COMPRISING-SI—SI-BRIDGE

(71) Applicant: ExxonMobil Chemical Patents Inc., Baytown, TX (US)

(72) Inventors: Jian Yang, Houston, TX (US); Matthew W. Holtcamp, Huffman, TX (US); Gregory S. Day, College Station, TX (US); Xiongdong Lian, Spring, TX (US); Xuan Ye, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/160,821

(22) Filed: May 20, 2016

(65) Prior Publication Data

US 2017/0015686 A1    Jan. 19, 2017

Related U.S. Application Data

(60) Provisional application No. 62/192,709, filed on Jul. 15, 2015.

(51) Int. Cl.
| | | |
|---|---|---|
| *C07F 17/00* | (2006.01) | |
| *C08F 4/6592* | (2006.01) | |
| *C08F 210/16* | (2006.01) | |
| *C08F 4/659* | (2006.01) | |

(52) U.S. Cl.
CPC .......... *C07F 17/00* (2013.01); *C08F 4/65927* (2013.01); *C08F 4/65912* (2013.01); *C08F 4/65916* (2013.01); *C08F 210/16* (2013.01)

(58) Field of Classification Search
CPC .. C07F 17/00; C08F 4/65927; C08F 4/65912; C08F 4/65916; C08F 210/16
See application file for complete search history.

(56) References Cited

U.S. PATENT DOCUMENTS

| | | | |
|---|---|---|---|
| 6,184,402 B1 | 2/2001 | Yamazaki et al. | |
| 6,376,407 B1 | 4/2002 | Burkhardt et al. | |
| 6,376,408 B1 | 4/2002 | Burkhardt et al. | |
| 6,376,409 B1 | 4/2002 | Burkhardt et al. | |
| 6,376,410 B1 | 4/2002 | Burkhardt et al. | |
| 6,376,411 B1 | 4/2002 | Burkhardt et al. | |
| 6,376,412 B1 | 4/2002 | Burkhardt et al. | |
| 6,376,413 B1 | 4/2002 | Kuchta et al. | |
| 6,376,627 B1 | 4/2002 | Burkhardt et al. | |
| 6,380,120 B1 | 4/2002 | Burkhardt et al. | |
| 6,380,121 B1 | 4/2002 | Kuchta et al. | |
| 6,380,123 B1 | 4/2002 | Kuchta et al. | |
| 6,380,124 B1 | 4/2002 | Burkhardt et al. | |
| 6,380,330 B1 | 4/2002 | Burkhardt et al. | |
| 6,380,331 B1 | 4/2002 | Kuchta et al. | |
| 6,380,334 B1 | 4/2002 | Kuchta et al. | |
| 6,399,723 B1 | 6/2002 | Burkhardt et al. | |
| 6,414,095 B1 | 7/2002 | Burkhardt et al. | |
| 6,426,395 B1 | 7/2002 | Yamazaki et al. | |
| 6,784,305 B2 | 8/2004 | Schulte et al. | |
| 6,825,372 B2 | 11/2004 | Burkhardt et al. | |
| 6,888,017 B2 | 5/2005 | Kuchta et al. | |
| 6,894,179 B2 | 5/2005 | Kuchta et al. | |
| 6,903,229 B2 | 6/2005 | Burkhardt et al. | |
| 6,936,675 B2 | 8/2005 | Szul et al. | |
| 7,157,531 B2 | 1/2007 | Szul et al. | |
| 7,405,261 B2 | 7/2008 | Schulte et al. | |
| 8,058,461 B2 | 11/2011 | Voskoboynikov et al. | |
| 8,609,793 B2 | 12/2013 | Buck et al. | |
| 2002/0123582 A1 | 9/2002 | Speca | |
| 2003/0088038 A1 | 5/2003 | Vaughan et al. | |
| 2014/0057777 A1 | 2/2014 | Buck et al. | |
| 2014/0107301 A1 | 4/2014 | Buck et al. | |

FOREIGN PATENT DOCUMENTS

| | | |
|---|---|---|
| EP | 2532687 | 12/2012 |
| JP | 2011-137146 | 7/2011 |
| WO | WO1998/403331 | 9/1998 |
| WO | WO2002/02576 | 1/2002 |
| WO | 2013/007650 | 1/2013 |
| WO | WO2013/151863 | 10/2013 |
| WO | 2016/094843 | 6/2016 |
| WO | 2016/171807 | 10/2016 |
| WO | 2016/172099 | 10/2016 |

OTHER PUBLICATIONS

Perez-Camacho, O. et al., "Si$_2$Me$_4$-bridged zirconocene dichlorides: crystal and molecular structure of meso-Si$_2$Me$_4$(3-SiMe$_3$—C$_9$H$_5$)$_2$ZrCl$_2$," Journal of Organometallic Chemistry, 1999, vol. 585, pp. 18-25.

Spaleck, W. et al., "Stereospecific Metallocene Catalysts Scope and Limits of Rational Catalyst Design," Macromolecular Symposia, 1995, vol. 89, pp. 237-247.

*Primary Examiner* — Caixia Lu

(57) ABSTRACT

This invention relates to novel bridged bis indenyl metallocene catalyst compounds where the bridge is —((R$^{15*}$)$_2$Si—Si(R$^{15}$)$_2$)— wherein, each R$^{15}$ and R$^{15*}$ is identical or different and is a substituted or unsubstituted, branched or unbranched C$_1$-C$_{20}$ alkyl group, preferably each R$^{15}$ together do not form a ring, and/or each R$^{15*}$ together do not form a ring, and/or R$^{15}$ and R$^{15*}$ together do not form a ring. This invention also relates to polymerization processes to produce polymer and to polymer compositions produced by the methods described.

36 Claims, 10 Drawing Sheets

Run Conditions and Instrument & Polymer Parameters

Analyzed as Polyethylene

Inject Mass (mg) = 0.1489

Calc. Mass (mg) = 0.141 (94.6%)

Adjusted Flow Rate (ml/m) = 0.552

Column Cal. C0 = 11.872

Column Cal. C1 = -0.29939

Column Cal. C2 = -0.0015608

Column Cal. C3 = 0

Inject Mark (ml) = 32.512

Vistalon B1 = 1.074

Linear Zimm Analysis

A2 (Input Value) = 0.0015

(dn/dc) = 0.1048

LS to DRI (ml) = 0.25

LS to Vis. (ml) = 0.48

K (sample) = 0.000579 alpha (sample) = 0.695

LS Calib. Const. = 4.6889e-05

DRI Const. = 0.0001263

DP Const. = 0.3298

IP Gain = 28.04 mV/KPa

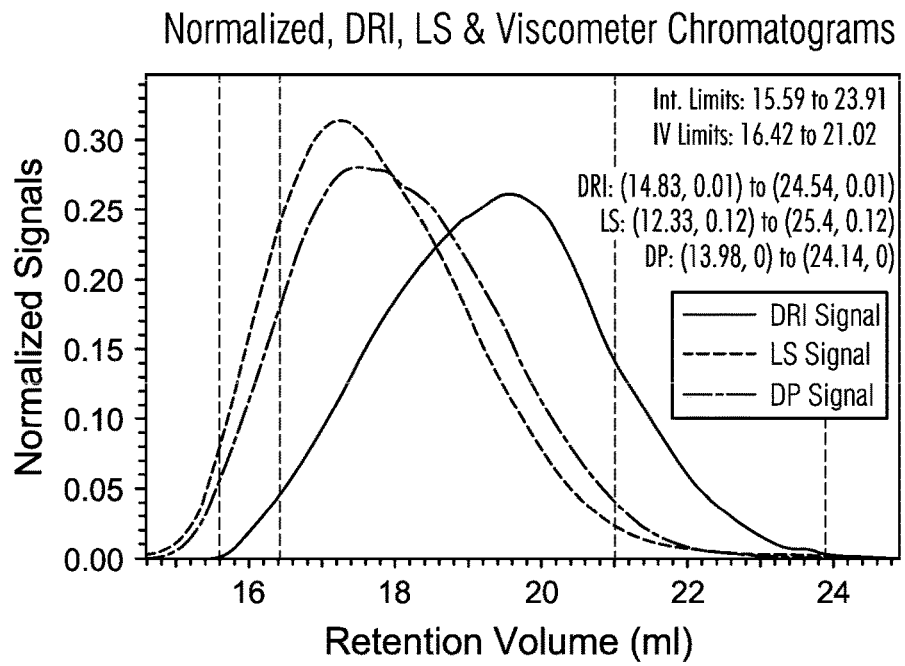

FIG. 10C

Run Conditions and Instrument & Polymer Parameters

Analyzed as ethylene-hexene copolymer with 2.5 weight percent comonomer

Inject Mass (mg) = 0.14
Calc. Mass (mg) = 0.13 (92.9%)
Adjusted Flow Rate (ml/m) = 0.552
Column Cal. C0 = 11.872
Column Cal. C1 = -0.29939
Column Cal. C2 = -0.0015608
Column Cal. C3 = 0
Inject Mark (ml) = 32.512
Vistalon B1 = 1.063

Linear Zimm Analysis
A2 (Input Value) = 0.0015
(dn/dc) = 0.1048
LS to DRI (ml) = 0.25
LS to Vis. (ml) = 0.48
K (sample) = 0.00056814
alpha (sample) = 0.695
LS Calib. Const. = 4.6889e-05
DRI Const. = 0.0001263
DP Const. = 0.3298
IP Gain = 28.04 mV/KPa

FIG. 10D

SUBSTITUTED BIS INDENYL METALLOCENE CATALYST COMPOUNDS COMPRISING-SI—SI-BRIDGE

CROSS REFERENCE TO RELATED APPLICATIONS

This invention claims priority to and the benefit of U.S. Ser. No. 62/192,709, filed Jul. 15, 2015.

FIELD OF THE INVENTION

This invention relates to novel catalyst compounds comprising —Si—Si— bridges, catalyst systems comprising such, and uses thereof.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization are often based on transition metal compounds, e.g., metallocenes, as catalyst precursors, which are activated either with the help of alumoxane, or with an activator containing a non-coordinating anion.

WO 2002/002576 discloses metallocene compositions and their use in the preparation of catalyst systems for olefin polymerization, particularly propylene polymerization. The bridged bis (2-$R^3$-4-phenyl-indenyl) metallocenes described therein include those wherein at least one of the phenyl rings is substituted at the 3' and 5' positions by butyl groups which may be the same or different, e.g., tert-butyl.

US 2014/0057777, US 2014/0107301, and WO 2013/151863 disclose $(Me_2Si)_2(Indenyl)_2ZrCl_2$.

US 2003/0088038 discloses $Me_2Si—O—SiMe_2(indenyl)_2ZrCl_2$.

Journal of Organometallic Chemistry, Vol. 585, 1999, pp. 18-25, discloses $Si_2Me_4$-bridged zirconocene dichlorides, such as meso-$(Me_2Si)_2(Indenyl)_2ZrCl_2$ and meso-$Si_2Me_4$(3-$SiMe_3$-$C_9H_5)_2ZrCl_2$.

Other references of interest include: JP2011-137146A; WO 98/403331; and U.S. Pat. Nos. 7,405,261; 6,784,305; 6,376,408; 6,903,229; 8,058,461; 6,888,017; 6,376,413; 6,894,179; 6,380,123; 6,380,121; 6,380,334; 6,380,331; 6,376,410; 6,903,229; 6,376,408; 6,376,627; 6,376,412; 6,825,372; 6,380,124; 6,399,723; 6,380,120; 6,376,407; 6,414,095; 6,376,409; 6,376,411; 6,380,330; 6,936,675; 7,157,531; and U.S. Pat. No. 8,609,793.

There is still a need in the art for new and improved catalyst systems for the polymerization of olefins, in order to achieve specific polymer properties, such as high melting point, high molecular weights, to increase conversion or comonomer incorporation, or to alter comonomer distribution without deteriorating the resulting polymer's properties.

SUMMARY OF THE INVENTION

This invention relates to a novel bridged transition metal complexes represented by the formula (I):

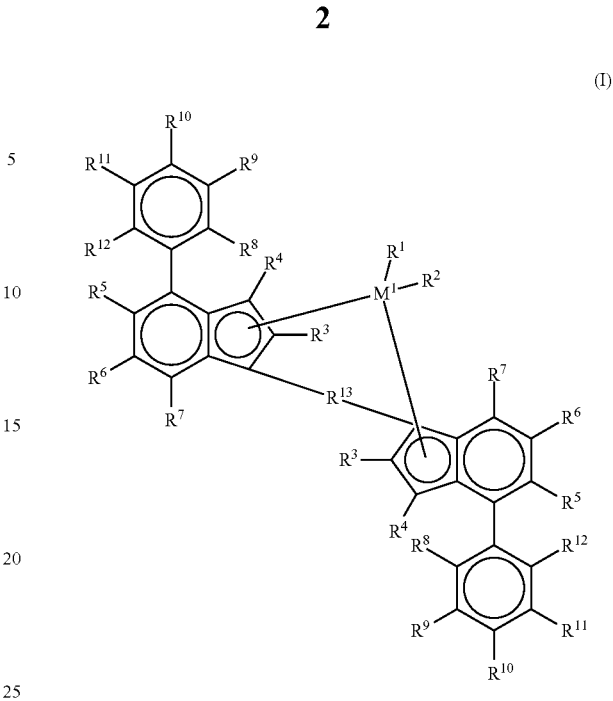

(I)

wherein $M^1$ is selected from the group consisting of titanium, zirconium, hafnium;

each $R^1$ and $R^2$ are identical or different and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ (preferably $C_8$-$C_{30}$) arylalkenyl group, an OH group or a halogen atom, or a conjugated diene which is, optionally, substituted with one or more hydrocarbyl, tri (hydrocarbyl) silyl groups or tri (hydrocarbyl) silylhydrocarbyl groups, said diene having up to 30 atoms not counting hydrogen;

each $R^3$ to $R^7$ are identical or different and are each a hydrogen atom, or a substituted or unsubstituted, branched or unbranched $C_1$-$C_{10}$ alkyl group which may be halogenated;

$R^{13}$ is —$((R^{15*})_2Si—Si(R^{15})_2)$— wherein, each $R^{15}$ and $R^{15*}$ is identical or different and is a substituted or unsubstituted, branched or unbranched $C_1$-$C_{20}$ alkyl group;

each $R^8$, $R^{10}$, and $R^{12}$ are identical or different and are each a hydrogen atom or a substituted or unsubstituted, branched or unbranched, $C_1$-$C_{10}$ alkyl group which may be halogenated; and each $R^9$ and $R^{11}$ are identical or different and are a hydrogen atom or a substituted or unsubstituted, branched or unbranched, $C_2$-$C_{20}$ alkyl group which may be halogenated.

In another aspect, embodiments of the invention provide an —Si—Si— bridged bis(4-phenyl-indenyl) transition metal complex wherein $R^3$ is a hydrogen atom and $R^9$ and $R^{11}$ are each t-butyl groups.

In another aspect of the invention, each $R^{15}$ together do not form a ring, and/or each $R^{15*}$ together do not form a ring, and/or $R^{15}$ and $R^{15*}$ together do not form a ring.

More particularly, embodiments of the invention provide a transition metal complex represented by the formula (I) above, wherein $M^1$ is Zr, Hf or Ti, $R^3$ is a hydrogen atom or a $C_1$-$C_{10}$ alkyl group, $R^8$, $R^{10}$, and $R^{12}$ are each hydrogen atoms and $R^9$ and $R^{11}$ are identical or different and are each a $C_3$-$C_{20}$ alkyl group.

In yet another aspect, embodiments of the invention provide a catalyst system comprising an activator and a transition metal complex as described herein.

In still another aspect, embodiments of the invention provide a polymerization process comprising: a) contacting one or more alkene monomers (such as ethylene) with a catalyst system comprising: i) an activator and ii) a transition metal complex described herein.

In still another aspect, embodiments of the invention provide a polymerization process to produce a polymer blend (preferably a bimodal polymer composition) comprising: a) contacting one or more alkene monomers (such as ethylene) with a catalyst system comprising: i) an activator, ii) a transition metal complex described above, and (iii) a second catalyst compound.

This invention further relates to polymer compositions produced by the methods described herein.

The catalysts and catalyst systems described herein provide polymers, such as polyethylene polymers wherein incorporation of comonomers, such as $C_3$ to $C_8$ alkylene monomers, is less than 20%, more preferably less than 15% and even more preferably less than 10% by weight of the copolymer and with high molecular weights while maintaining good catalyst activities.

Thus, the embodiments described herein pertain to novel catalyst compounds, catalysts systems comprising such compounds, and processes for the polymerization of olefins using such compounds and systems.

BRIEF DESCRIPTION OF THE FIGURES

FIGS. 10A, 10B, 10C, and 10D are the GPC of ethylene 1-hexene copolymers made by Catalyst 10 (Table 3, Run 2).

DETAILED DESCRIPTION OF THE INVENTION

Figure 1:
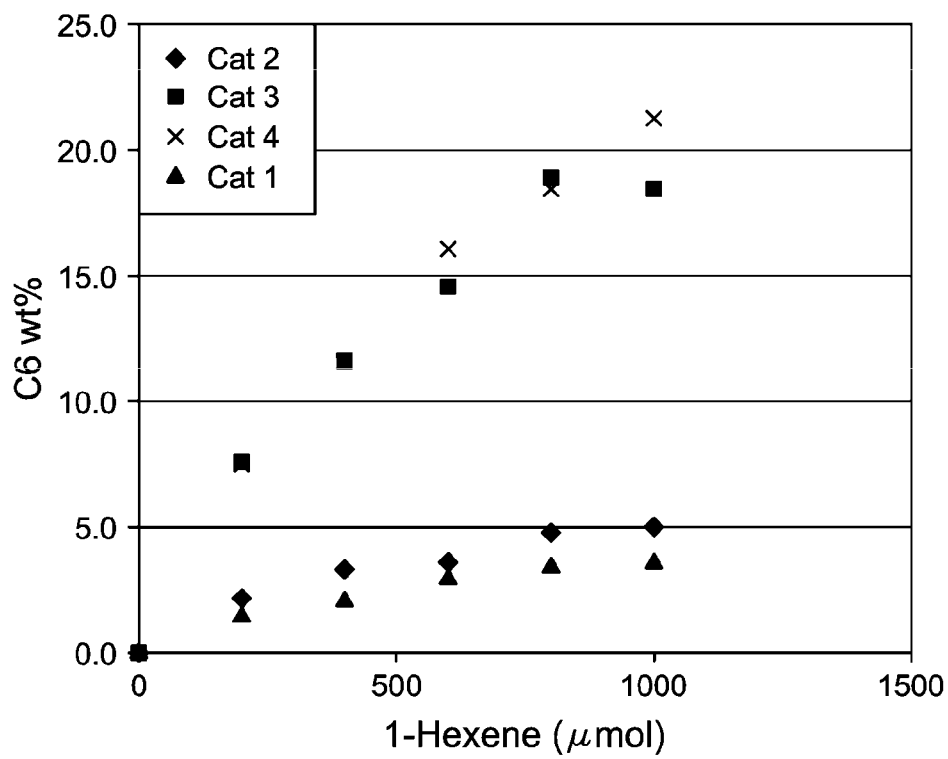
FIG. 1 is a representative plot of 1-hexene Incorporation (C6 wt %) vs 1-hexene Loading for Catalyst 1 in comparison to Catalysts 2-4 in Table 1.

For the purposes of this invention and the claims thereto, the new numbering scheme for the Periodic Table Groups is used as described in CHEMICAL AND ENGINEERING NEWS, 63(5), pg. 27 (1985). Therefore, a "group 4 metal" is an element from group 4 of the Periodic Table, e.g., Hf, Ti, or Zr.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

"Catalyst productivity" is a measure of how many grams of polymer (P) are produced using a polymerization catalyst comprising W g of catalyst (cat), over a period of time of T hours; and may be expressed by the following formula: $P/(T \times W)$ and expressed in units of $gPgcat^{-1}hr^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kgP/molcat).

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" is used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

For purposes of this invention and claims thereto, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group.

As used herein, Mn is number average molecular weight, Mw is weight average molecular weight, and Mz is z average molecular weight, wt % is weight percent, and mol % is mole percent. Molecular weight distribution (MWD), also referred to as polydispersity (PDI), is defined to be Mw divided by Mn. Unless otherwise noted, all molecular weight units (e.g., Mw, Mn, Mz) are g/mol.

Unless otherwise noted all melting points (Tm) are DSC second melt.

The following abbreviations may be used herein: dme is 1,2-dimethoxyethane, Me is methyl, Ph is phenyl, Et is ethyl, Pr is propyl, iPr is isopropyl, n-Pr is normal propyl, Bu is butyl, cPR is cyclopropyl, iBu is isobutyl, tBu is tertiary butyl, p-tBu is para-tertiary butyl, nBu is normal butyl, sBu is sec-butyl, TMS is trimethylsilyl, TIBAL is triisobutylaluminum, TNOAL is tri(n-octyl)aluminum, MAO is methylalumoxane, p-Me is para-methyl, Ph is phenyl, Bn is benzyl (i.e., $CH_2Ph$), THF (also referred to as thf) is tetrahydrofuran, RT is room temperature (and is 23° C. unless otherwise indicated), tol is toluene, EtOAc is ethyl acetate, and Cy is cyclohexyl.

A "catalyst system" comprises at least one catalyst compound and at least one activator. When "catalyst system" is used to describe such the catalyst compound/activator combination before activation, it means the unactivated catalyst complex (precatalyst) together with an activator and, optionally, a co-activator. When it is used to describe the combination after activation, it means the activated complex and the activator or other charge-balancing moiety. The transition metal compound may be neutral as in a precatalyst, or a charged species with a counter ion as in an activated catalyst system. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the metallocene catalyst may be described as a catalyst precursor, a pre-catalyst compound, metallocene catalyst compound or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. Activators containing non-coordinating anions can also be referred to as stoichiometric activators. A stoichiometric activator can be either neutral or ionic. The terms ionic activator and stoichiometric ionic activator can be used interchangeably. Likewise, the terms neutral stoichiometric activator and Lewis acid activator can be used interchangeably. The term non-coordinating anion activator includes neutral stoichiometric activators, ionic stoichiometric activators, ionic activators, and Lewis acid activators.

A metallocene catalyst is defined as an organometallic compound with at least one π-bound cyclopentadienyl moiety (or substituted cyclopentadienyl moiety) and more frequently two π-bound cyclopentadienyl moieties or substituted cyclopentadienyl moieties.

For purposes of this invention and claims thereto in relation to metallocene catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group.

The terms "hydrocarbyl radical," "hydrocarbyl," "hydrocarbyl group," "alkyl radical," and "alkyl" are used interchangeably throughout this document. Likewise, the terms "group," "radical," and "substituent" are also used interchangeably in this document. For purposes of this disclosure, "hydrocarbyl radical" is defined to be C1-C100 radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted hydrocarbyl radicals are radicals in which at least one hydrogen atom of the hydrocarbyl radical has been substituted with at least one halogen (such as Br, Cl, F or I) or at least one functional group such as NR*2, OR*, SeR*, TeR*, PR*2, AsR*2, SbR*2, SR*, BR*2, SiR*3, GeR*3, SnR*3, PbR*3, and the like, or where at least one heteroatom has been inserted within a hydrocarbyl ring.

The term "alkenyl" means a straight-chain, branched-chain, or cyclic hydrocarbon radical having one or more double bonds. These alkenyl radicals may be optionally substituted. Examples of suitable alkenyl radicals include, but are not limited to, ethenyl, propenyl, allyl, 1,4-butadienyl cyclopropenyl, cyclobutenyl, cyclopentenyl, cyclohexenyl, cyclooctenyl, and the like, including their substituted analogues.

The term "alkoxy" or "alkoxide" means an alkyl ether or aryl ether radical wherein the term alkyl is as defined above. Examples of suitable alkyl ether radicals include, but are not limited to, methoxy, ethoxy, n-propoxy, iso-propoxy, n-butoxy, iso-butoxy, sec-butoxy, tert-butoxy, phenoxyl, and the like.

The term "aryl" or "aryl group" means a six carbon aromatic ring and the substituted variants thereof, including but not limited to, phenyl, 2-methyl-phenyl, xylyl, 4-bromoxylyl. Likewise heteroaryl means an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom-substituted ring.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng. Chem. Res., 2000, Vol. 29, p. 4627.

A bulk polymerization means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

Transition Metal Complexes

In particular embodiments the invention relates to novel bridged metallocene transition metal complexes, where the complexes include at least one indenyl ligand substituted at the 4-position with a phenyl group, the phenyl group being substituted at the 3' and 5' ($R^9$ and $R^{11}$) positions with particular combinations of substituents and bridged with an —Si—Si— group. In preferred embodiments, the $R^9$ and $R^{10}$ positions of the phenyl ring are selected to be sterically hindering (e.g., branched hydrocarbyl groups).

In a preferred embodiment this invention relates to a catalyst compound, and catalyst systems comprising such compounds, represented by the formula (I):

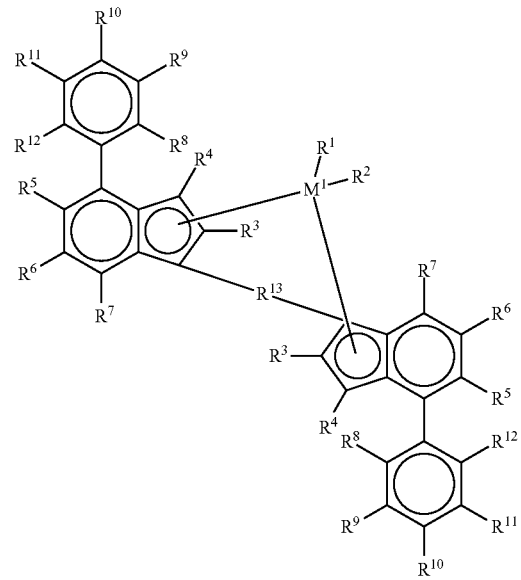

(I)

wherein $M^1$ is selected from the group consisting of titanium, zirconium, hafnium (preferably zirconium and hafnium, preferably zirconium);

each $R^1$ and $R^2$ are identical or different, and are each a hydrogen atom or a substituted or unsubstituted, branched or unbranched $C_1$-$C_{20}$ alkyl group;

each $R^3$ to $R^7$ are identical or different and are each a hydrogen atom, or a substituted or unsubstituted, branched or unbranched $C_1$-$C_{10}$ alkyl group which may be halogenated;

$R^{13}$ is —$((R^{15*})_2Si$—$Si(R^{15})_2)$— wherein, each $R^{15}$ and $R^{15*}$ is identical or different and is a substituted or unsubstituted, branched or unbranched $C_1$-$C_{20}$ alkyl group (preferably each $R^{15}$ together do not form a ring, and/or each $R^{15*}$ together do not form a ring, and/or $R^{15}$ and $R^{15*}$ together do not form a ring);

each $R^8$, $R^{10}$ and $R^{12}$ are identical or different and are each a hydrogen atom or a substituted or unsubstituted, branched or unbranched $C_1$-$C_{10}$ alkyl group which may be halogenated; and each $R^9$ and $R^{11}$ are identical or different and are a hydrogen atom or a substituted or unsubstituted, branched or unbranched $C_2$-$C_{20}$ alkyl group which may be halogenated.

In a preferred embodiment of the invention in any embodiment of any formula described herein, $M^1$ is Hf, Zr or Ti, preferably Hf or Zr, preferably Zr.

In a preferred embodiment of the invention in any embodiment of any formula described herein, each $R^{15}$ is preferably a methyl, ethyl, propyl, butyl, pentyl, hexyl, heptyl, octyl, nonyl, decyl, undecyl, or dodecyl group.

In a preferred embodiment of the invention in any embodiment of any formula described herein, each $R^{15*}$ is preferably a methyl, ethyl, propyl, butyl, pentyl, hexyl, heptyl, octyl, nonyl, decyl, undecyl, or dodecyl group.

In a preferred embodiment of the invention in any embodiment of any formula described herein, $R^{13}$ is represented by the formula —$((R^{15*})_2Si$—$Si(R^{15})_2)$—, and each $R^{15}$ and $R^{15*}$ is, independently, a $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl. Preferably, $R^{13}$ is the bridging group -(Me$_2$)Si—Si(Me$_2$)—.

In a preferred embodiment of the invention in any embodiment of any formula described herein each $R^{15}$ together do not form a ring and each $R^{15*}$ together do not form a ring.

In a preferred embodiment of the invention in any embodiment of any formula described herein, each $R^{15}$ together do not form a ring.

In a preferred embodiment of the invention in any embodiment of any formula described herein, $R^{15}$ and $R^{15*}$ together do not form a ring.

In a preferred embodiment of the invention in any embodiment of any formula described herein, each $R^{15}$ together do not form a ring, and each $R^{15*}$ together do not form a ring, and $R^{15}$ and $R^{15*}$ together do not form a ring.

In an alternate embodiment, in any formula described herein, each $R^1$ and $R^2$ is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, ($R^1$ and $R^2$ may form a part of a fused ring or a ring system), preferably each $R^1$ and $R^2$ is independently selected from halides and $C_1$ to $C_5$ alkyl groups (preferably methyl groups). Preferably $R^1$ and $R^2$ are selected from chloro, bromo, methyl, ethyl, propyl, butyl, pentyl, hexyl, heptyl, octyl, nonyl, decyl, undecyl, and dodecyl.

Alternatively, $R^1$ and $R^2$ may also be joined together to form an alkanediyl group or a conjugated $C_4$-$C_{40}$ diene ligand which is coordinated to M in a metallocyclopentene fashion; $R^1$ and $R^2$ may also be identical or different conjugated dienes, optionally substituted with one or more hydrocarbyl, tri (hydrocarbyl) silyl groups or tri (hydrocarbyl) silylhydrocarbyl groups, said dienes having up to 30 atoms not counting hydrogen and forming a π-complex with $M^1$.

Exemplary groups suitable for $R^1$ and or $R^2$ include 1,4-diphenyl, 1,3-butadiene, 1,3-pentadiene, 2-methyl 1,3-pentadiene, 2,4-hexadiene, 1-phenyl, 1,3-pentadiene, 1,4-dibenzyl, 1,3-butadiene, 1,4-ditolyl-1,3-butadiene, 1,4-bis (trimethylsilyl)-1,3-butadiene, and 1,4-dinaphthyl-1,3-butadiene; preferably $R^1$ and $R^2$ are identical and are a $C_1$-$C_3$ alkyl or alkoxy group, a $C_6$-$C_{10}$ aryl or aryloxy group, a $C_2$-$C_4$ alkenyl group, a $C_7$-$C_{10}$ arylalkyl group, a $C_7$-$C_{12}$ alkylaryl group, or a halogen atom, particularly chlorine.

In any embodiment of the invention, the 2 position of the indenyl group or groups, e.g., $R^3$ in formula I, may be selected from hydrogen, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, or a substituted or unsubstituted phenyl, particularly methyl, ethyl, n-propyl, isopropyl, n-butyl, isobutyl, sec-butyl, tert-butyl, more particularly hydrogen or methyl.

In any embodiment of the invention, the 2 position of the indenyl group or groups, e.g., $R_3$ in formula I, is hydrogen.

In any embodiment of the invention, $R^4$, $R^5$, $R^6$, and $R^7$ of formula I may be identical or different and are each a hydrogen atom, a halogen atom, a $C_1$-$C_{10}$ alkyl group (methyl, ethyl, propyl, butyl, pentyl, hexyl, heptyl, octyl, nonyl, decyl, undecyl, dodecyl or an isomer thereof) which may be halogenated, or a $C_6$-$C_{10}$ aryl group which may be halogenated.

In any embodiment of the invention, $R^8$, $R^{10}$ and $R^{12}$ of formula I may be identical or different and are each a hydrogen atom, a halogen atom, a $C_1$-$C_{10}$ alkyl group (preferably $C_2$ to $C_{10}$, preferably $C_3$ to $C_{10}$, preferably methyl, ethyl, propyl, butyl, pentyl, hexyl, heptyl, octyl, nonyl, decyl, undecyl, dodecyl or an isomer thereof) which may be halogenated, a $C_6$-$C_{10}$ aryl group which may be halogenated, preferably methyl, ethyl, propyl, butyl, pentyl, hexyl, phenyl, octyl, nonyl, decyl, undecyl, dodecyl, preferably methyl, ethyl, or phenyl.

In any embodiment of the invention, $R^9$ and $R^{11}$ of formula I are identical or different and selected from a hydrogen atom, $C_2$-$C_{20}$ alkyl group (preferably $C_3$ to $C_{16}$, preferably $C_4$ to $C_{12}$, preferably butyl, pentyl, hexyl, heptyl, octyl, nonyl, decyl, undecyl, dodecyl and isomers thereof) which may be halogenated, a $C_6$-$C_{10}$ aryl group which may be halogenated. In some embodiments, $R^9$ and $R^{11}$ may be the same or different and are each a butyl group, an aryl group, an isopropyl group, or a fluoroalkyl group, particularly wherein each of $R^9$ and $R^{11}$ is selected from the group consisting of propyl, isopropyl, n-propyl, n-butyl-, iso-butyl-, and tert-butyl groups.

In an alternate embodiment, $R^9$ and $R^{11}$ may be the same or different and are each a butyl group, an aryl group, an isopropyl group, or a fluoroalkyl group, particularly wherein each of $R^9$ and $R^{11}$ is selected from the group consisting of propyl, isopropyl, n-propyl, n-butyl-, iso-butyl-, and tert-butyl groups and $R^{10}$ may be —NR'$_2$, —SR', —OR', —OSiR'$_3$, or a —PR'$_2$ radical, wherein R' is one of a hydrogen atom, halogen atom, a $C_1$-$C_{10}$ alkyl group, or a $C_6$-$C_{10}$ aryl group, particularly wherein $R^{10}$ is OR' wherein R' is a $C_1$-$C_{10}$ alkyl group, particularly a methoxy, ethoxy, n-propoxy, isopropoxy, n-butoxy, iso-butoxy, sec-butoxy, or t-butoxy group, most particularly methoxy.

In some embodiments, $R^3$ is a hydrogen atom and each of $R^9$ and $R^{11}$ is one of n-butyl-, iso-butyl-, and particularly tert-butyl groups.

In another embodiment, $R^3$ is a hydrogen atom, each of $R^9$ and $R^{11}$ is a hydrogen atom and $R^8$, $R^{10}$ and $R^{12}$ are each hydrogen atoms.

In yet another embodiment, $R^3$ is a hydrogen atom or a substituted or unsubstituted, branched or unbranched $C_1$-$C_{10}$ alkyl group and each of $R^9$ and $R^{11}$ is a substituted or unsubstituted, branched or unbranched $C_1$-$C_{20}$ alkyl group, preferably a $C_2$-$C_{20}$ alkyl group.

In still other embodiments, le is the bridging group -(Me$_2$)Si—Si(Me$_2$)—.

Particularly useful transition metal complexes are Zr-based or Hf-based complexes. Additionally, some such transition metal complexes are bridged by a dialkyldisiladiyl group.

Particularly preferred transition metal complexes of the present invention are represented the formula (I) above, wherein $M^1$ is selected from the group consisting of titanium, zirconium, and hafnium, particularly zirconium or hafnium, more typically zirconium; $R^1$ and $R^2$ are identical or different, and are one of a hydrogen atom, a $C_1$-$C_{10}$ alkyl group (preferably methyl, ethyl, butyl, pentyl, hexyl, heptyl, octyl, nonyl, decyl, undecyl, dodecyl and isomers thereof), or a halogen atom (preferably Cl, Br, F or I).

In particular embodiments complexes according to formula (I), the $R^3$ groups may be identical or different and are each a hydrogen atom, a $C_1$-$C_{10}$ alkyl group (preferably $C_2$ to $C_{10}$, preferably $C_3$ to $C_8$, preferably methyl, ethyl, butyl, pentyl, hexyl, heptyl, octyl, nonyl, decyl, undecyl, dodecyl or an isomer thereof) which may be halogenated, a $C_6$-$C_{10}$ aryl group which may be halogenated. In some embodiments, each $R^3$ may be the same or different and are each a $C_1$-$C_{10}$ alkyl group. In particular embodiments, $R^3$ is not a hydrogen atom, e.g., in particular embodiments, each $R^3$ is identical and is a $C_1$-$C_4$ alkyl group which may be halogenated.

In a preferred embodiment, in formula (I), the $R^4$ to $R^7$ groups are identical or different and may be hydrogen or a $C_1$-$C_{10}$ alkyl group (preferably methyl, ethyl, butyl, pentyl, hexyl, heptyl, octyl, nonyl, decyl, undecyl, dodecyl or an isomer thereof) which may be halogenated. In particular embodiments, two or more adjacent radicals $R^5$ to $R^7$ together with the atoms connecting them form one or more rings, preferably a 6-membered ring, preferably 4, 5, 6, 7 or 8 membered ring.

In a preferred embodiment, in formula (I) $R^{13}$ is —(R")$_2$Si—Si(R")$_2$— wherein the R" groups may be the same or different and are each selected from a hydrogen or a $C_1$-$C_{10}$ alkyl group, preferably a $C_1$-$C_2$ alkyl group (e.g., methyl or ethyl).

In a preferred embodiment, in formula (I), each $R^9$ and $R^{11}$ may be identical or different and are each a $C_2$-$C_{20}$ alkyl group which may be halogenated. In particular embodiments according to formula (I), each $R^9$ and each $R^{11}$ is selected from the group consisting of primary, secondary or tertiary butyl groups, isopropyl groups, fluoroalkyl groups, preferably a tertiary butyl group, particularly n-butyl-, iso-butyl-, and tert-butyl groups.

More specifically, in certain embodiments, each $R^1$ and $R^2$ may be the same or different and are each a halogen atom, preferably Cl; each $R^3$ may be the same or different and are each a hydrogen atom or a $C_1$-$C_{10}$ alkyl group, preferably methyl; each $R^4$, $R^5$, $R^6$, and $R^7$ may be the same or different and are each a hydrogen atom or $C_1$-$C_{10}$ alkyl group, preferably each is a hydrogen atom; each $R^8$ and $R^{12}$ are each a hydrogen atom; $R^{13}$ is —(R")$_2$Si—Si(R")$_2$— wherein each R" may be the same or different and are each a hydrogen or $C_1$-$C_{10}$ alkyl group, preferably methyl; each $R^9$ and $R^{11}$ is a $C_2$-$C_{10}$ alkyl group, particularly a tert-butyl group; and wherein each $R^{10}$ is hydrogen or a $C_1$-$C_{10}$ alkyl group.

In particular embodiments, transition metal complexes according to formula (I) include those wherein $R^1$ and $R^2$ are chlorine; each $R^3$ is a hydrogen atom; each $R^4$, $R^5$, $R^6$, and $R^7$, $R^8$, $R^{10}$ and $R^{12}$ are hydrogen; $R^{13}$ is —(CH$_3$)$_2$Si—Si(CH$_3$)$_2$—, and each $R^9$ and $R^{11}$ is a tert-butyl group. In particular, $M^1$ is zirconium.

In particular embodiments, transition metal complexes according to formula (I) include those wherein each $M^1$ is zirconium, $R^1$ and $R^2$ are chlorine; each $R^3$ is a hydrogen atom; each $R^4$, $R^5$, $R^6$, and $R^7$, $R^8$, $R^{10}$, and $R^{12}$ are hydrogen; $R^{13}$ is —(CH$_3$)$_2$Si—Si(CH$_3$)$_2$—, and each $R^9$ and $R^{11}$ is a hydrogen atom. In particular, $M^1$ is zirconium.

In particular embodiments, transition metal complexes according to formula (I) include those wherein $R^1$ and $R^2$ are chlorine; each $R^3$ is a $C_1$-$C_{10}$ alkyl group; each $R^4$, $R^5$, $R^6$, and each $R^7$, $R^8$, $R^{10}$, and $R^{12}$ are hydrogen; $R^{13}$ is —(CH$_3$)$_2$Si—Si(CH$_3$)$_2$—, and each $R^9$ and $R^{11}$ is a tert-butyl group. In particular, $M^1$ is zirconium.

The following particular zirconium-containing metallocenes and their hafnium-containing analogs are expressly disclosed: rac-tetramethyldisilylene bis(4-(3',5'-di-tert-butylphenyl)-indenyl) zirconium dichloride, meso-tetramethyldisilylene bis(4-(3',5'-di-tert-butylphenyl)-indenyl) zirconium dichloride.

Likewise, while the dichloro-substituted compounds (—ZrCl$_2$ and —HfCl$_2$) are enumerated above, the compounds where each of the chloride are replaced with methyl groups (e.g., —Zr((CH$_3$)$_2$ and —Hf(CH$_3$)$_2$)) are also expressly disclosed. And while the complexes above are substituted at the 2-position of the indene ring, analogs wherein the substitution occurs instead at the 1, 3, 4, 5, 6, and/or 7 position of the indene ring are also envisioned.

In particular embodiments, the rac/meso ratio of the metallocene catalyst is 50:1 or greater, or 40:1 or greater, or 30:1 or greater, or 20:1 or greater, or 15:1 or greater, or 10:1 or greater, or 7:1 or greater, or 5:1 or greater.

In an embodiment of the invention, the metallocene catalyst comprises greater than 55 mol % of the racemic isomer, or greater than 60 mol % of the racemic isomer, or greater than 65 mol % of the racemic isomer, or greater than 70 mol % of the racemic isomer, or greater than 75 mol % of the racemic isomer, or greater than 80 mol % of the racemic isomer, or greater than 85 mol % of the racemic isomer, or greater than 90 mol % of the racemic isomer, or greater than 92 mol % of the racemic isomer, or greater than 95 mol % of the racemic isomer, or greater than 98 mol % of the racemic isomer, based on the total amount of the racemic and meso isomer-if any, formed. In a particular embodiment of the invention, the bridged bis(indenyl)metallocene transition metal compound formed consists essentially of the racemic isomer.

In one aspect, an advantage is provided in that the need for the separation of meso from rac isomers is not required for the catalysts disclosed herein. In certain aspects, the meso isomer is more active than the rac isomer.

Amounts of rac and meso isomers are determined by proton NMR. $^1$H NMR data are collected at 23° C. in a 5 mm probe using a 400 MHz Bruker spectrometer with deuterated benzene or deuterated chloroform. Data is recorded using a maximum pulse width of 45°, 8 sec. between pulses and signal averaging 16 transients. The spectrum is normalized to protonated benzene in the deuterated benzene, which is expected to show a peak at 7.16 ppm.

In a preferred embodiment in any of the processes described herein, one catalyst compound is used, e.g., the catalyst compounds are not different. For purposes of this invention one metallocene catalyst compound is considered different from another if they differ by at least one atom. For example, "bisindenyl zirconium dichloride" is different from "(indenyl)(2-methylindenyl) zirconium dichloride" which is different from "(indenyl)(2-methylindenyl) hafnium dichloride." Catalyst compounds that differ only by isomer are considered the same for purposes if this invention, e.g., rac-dimethylsilylbis(2-methyl 4-phenyl)hafnium dimethyl is considered to be the same as meso-dimethylsilylbis(2-methyl 4-phenyl)hafnium dimethyl.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds are preferably chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an $X_1$ or $X_2$ ligand which is not a hydride, hydrocarbyl, or substituted hydrocarbyl, then the alumoxane should be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Methods to Prepare the Catalyst Compounds

The following is a generic scheme to prepare the catalysts described herein and further exemplified in the examples. Generally, metallocenes of this type are synthesized as shown below where (i) is a deprotonation via a metal salt of alkyl anion (e.g., "BuLi) to form an indenide; (ii) reaction of indenide with an appropriate bridging precursor (e.g., ClMe$_2$SiSiMe$_2$Cl); (iii) double deprotonation via an alkyl anion (e.g., "BuLi) to form a dianion; (iv) reaction of the dianion with a metal halide (e.g., ZrCl$_4$); and (v). The final products are obtained by crystallization separation of the crude solids.

polymerization. The catalyst systems may also be added to or generated in solution polymerization or bulk polymerization (in the monomer). The catalyst system typically comprise a complex as described above and an activator such as alumoxane or a non-coordinating anion.

Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing non-coordinating or weakly coordinating anion.

Alumoxane Activators

In one embodiment, alumoxane activators are utilized as an activator in the catalyst system. Alumoxanes are generally oligomeric compounds containing —Al(R$^1$)—O— subunits, where R$^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable

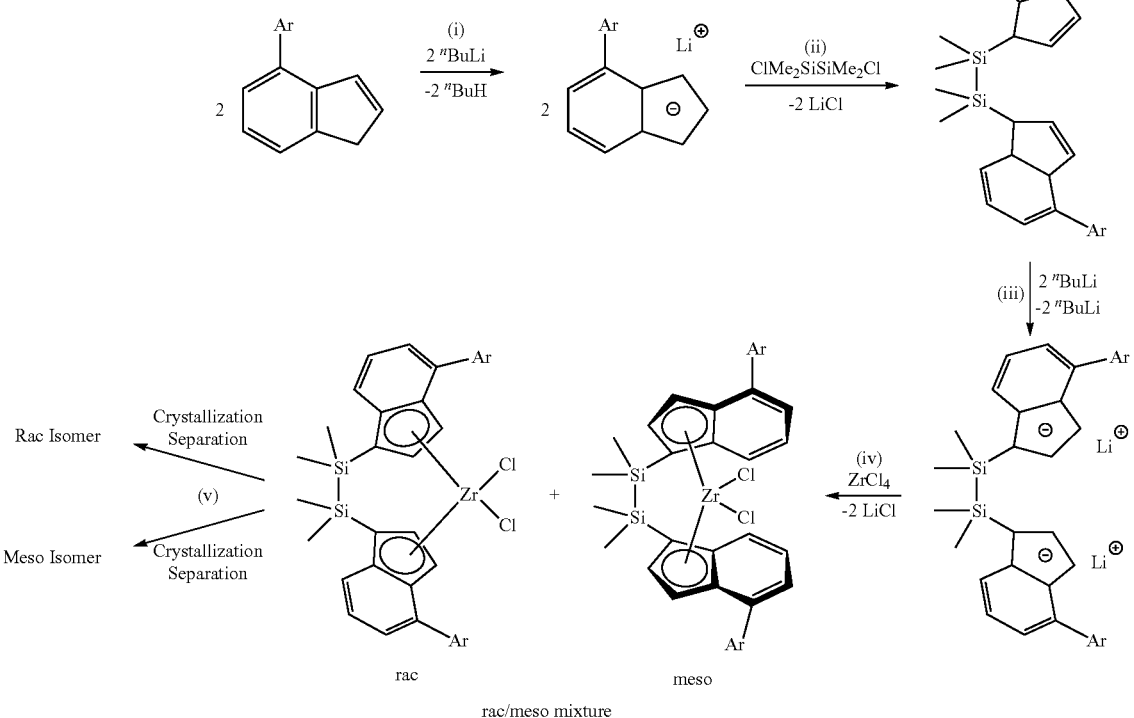

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any manner known from the literature including by supporting them for use in slurry or gas phase ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

Non-Coordinating Anion Activators

A non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient liability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment boron containing NCA activators represented by the formula below can be used:

where: Z is (L-H) or a reducible Lewis acid; L is a neutral Lewis base; H is hydrogen; (L-H) is a Bronsted acid; $A^{d-}$ is a boron containing non-coordinating anion having the charge d−; d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted C1 to C40 hydrocarbyl), preferably the reducible Lewis acids in formula (14) above as "Z" include those represented by the formula: $(Ph_3C)$, where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiums from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ ($A^{d-}$) is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5- bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

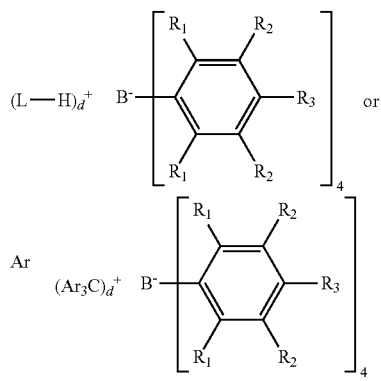

where:
each $R_1$ is, independently, a halide, preferably a fluoride;
Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); and
L is a neutral Lewis base; (L-H)$^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3$V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$], 1-(4-(tris(pentafluorophenyOborate)-2,3,5,6-tetrafluorophenyl)pyrrolidinium, and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, and triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl) phenyl)borate, and di-(i-propyl)ammonium tetrakis(pentafluorophenyl)borate (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1, alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. No. 5,153,157; U.S. Pat. No. 5,453,410; EP 0 573 120 B1; WO 94/07928; and WO 95/14044 which discuss the use of an alumoxane in combination with an ionizing activator).

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, pentyl, hexyl octyl or an isomer thereof) or a combination thereof, such as diethyl zinc, methylalumoxane, trimethylaluminum, triisobutylaluminum, trioctylaluminum, or a combination thereof.

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2$/$Al_2O_3$.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 µm. More preferably, the surface area of the support material is in the range of from about 50 to about 500 m$^2$/g, pore volume of from about 0.5 to about 3.5 cc/g and average particle size of from about 10 to about 200 µm. Most preferably, the surface area of the support material is in the range is from about 100 to about 400 m$^2$/g, pore volume from about 0.8 to about 3.0 cc/g and average particle size is from about 5 to about 100 µm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m$^2$/gm; pore volume of 1.65 cm$^3$/gm). Preferred silicas are marketed under the tradenames of DAVISON 952 or DAVISON 955 by the Davison Chemical Division of W. R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hrs. to about 24 hrs., from about 2 hrs. to about 16 hrs., or from about 4 hrs. to about 8 hrs. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hrs. to about 24 hrs., from about 2 hrs. to about 16 hrs., or from about 4 hrs. to about 8 hrs. The slurry of the supported metallocene compound is then contacted with the activator solution.

The mixture of the metallocene, activator and support is heated to about 0° C. to about 70° C., preferably to about 23° C. to about 60° C., preferably at room temperature. Contact times typically range from about 0.5 hrs. to about 24 hrs., from about 2 hrs. to about 16 hrs., or from about 4 hrs. to about 8 hrs.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Flourided Support

In an embodiment, this invention uses a founded (also referred to as flouridated) support. The founded supports (such as founded silica) can be obtained through the addition of a solution of polar solvent (such as water) and fluorine compound (such as $(NH_4)_2SiF_6$) to a slurry of support (such as a toluene slurry of silica). This preparation method contributes to an even distribution of the fluoride compound (such as $(NH_4)_2SiF_6$) onto the support surface (such as the silica surface), in contrast to a less homogeneous distribution observed when the solid salt is combined with the solid silica as described in US 2002/0123582 A1.

In an embodiment, an aqueous solution of fluorinating agent (such as $(NH_4)_2SiF_6$) is added to a slurry of support (such as a toluene slurry of silica). Vigorous stirring of the mixture allows the dissolved fluorine compound (in water) to be evenly absorbed onto the hydrophilic support surface. After filtration, the wet support is allowed to air dry until it is free flowing, and then may be calcined (typically at temperatures over 100° C. for at least 1 hr.).

In an embodiment, a solution of polar solvent and fluorinating agent (such as $(NH_4)_2SiF_6$) is added to a slurry of support (such as a toluene slurry of silica). Vigorous stirring of the mixture allows the dissolved fluorine compound (in water) to be evenly absorbed onto the hydrophilic support surface. After filtration, the wet support is allowed to air dry until it is free flowing, and then may be calcined (typically at temperatures over 100° C. for at least 1 hr.).

In a particularly useful embodiment of the invention, the catalyst systems described herein are prepared by:

1. Fluorided silica preparation: The wet method typically employs a minimal amount of a polar solvent (e.g., water, methanol, ethanol, isopropanol, or any solvent capable of dissolving the fluoride compound (such as ammonium hexafluorosilicate)) to dissolve the fluorinating agent (such as ammonium hexafluorosilicate), but can use an excess of solvent if desired. The solution (typically ammonium hexafluorosilicate solution) is then added to a slurry of silica in a non-polar solvent (e.g., toluene, or benzene, chloroform, etc.), followed by vigorous stirring of the resulting mixture. The polar/hydrophilic nature of the fluorinating agent (such as ammonium hexafluorosilicate) leads to its absorption onto the hydrophilic silica surface. When the non-polar solvent is removed (by filtration), silica with an even distribution of fluorinating agent (such as ammonium hexafluorosilicate) is obtained, and ready for subsequent drying and calcination steps.

2a. Immobilization of alumoxane on fluorided silica: In a preferred embodiment of the invention, the fluorided support material is then slurried in a non-polar solvent and the resulting slurry is contacted with a solution of alumoxane (such as methylalumoxane). The fluorided support/alumoxane mixture is then heated to elevated temperature (30° C. to 120° C., preferably, 80-100° C.) with vigorous stirring for a period of time (0.1 to 24 hrs., preferably, 1 to 3 hrs.). The support/activator is isolated by filtration, rinsed with non-polar solvent (e.g., toluene, pentane, hexane, etc.), and dried. The isolated support/activator is then slurried in a non-polar solvent (e.g., toluene), and a solution of metallocene compound/compounds is then contacted with the support/activator slurry. Vigorous stirring is typically applied.

2b. Immobilization of fluorided silica in solid form: In an alternate embodiment of the invention, the fluorided support material may be slowly added in solid form to a solution of alumoxane in non-polar solvent (e.g., toluene) (typically at room temperature) with vigorous stirring. This addition sequence, namely slow and portion-wise addition of fluorided silica to the alumoxane solution, is referred to as "reversed addition". After the addition of fluorided silica is completed, the fluorided support/alumoxane mixture is then heated to elevated temperature (30° C. to 120° C., preferably, 80 to 100° C.) with vigorous stirring for a period of time (0.1 to 24 hrs., preferably, 1 to 3 hrs.). The support/activator is then isolated by filtration, rinsed with non-polar solvent (e.g., toluene, pentane, hexane, etc.), and dried. The isolated support/activator is then slurried in a non-polar solvent (e.g., toluene), and a solution of metallocene compound/compounds is then contacted with the support/activator slurry. Vigorous stirring is typically applied. Under otherwise identical conditions, the reversed addition method for immobilizing MAO on fluorided silica surface offers higher polymerization activity for a wide variety of catalysts, compared to the "traditional addition" method where methylalumoxane solution is added to a slurry of fluorided silica in non-polar solvent.

3. Activation and supportation of metallocene on silica/MAO support: The silica/MAO support/activator generated in the MAO immobilization step 2 (a or b) is slurried in a non-polar solvent (e.g., toluene). The resulting slurry is then contacted with a solution of metallocene (one metallocene precursor or more) with vigorous stirring. The mixture is stirred for 0.5 hr. to 24 hrs. (preferably, for 1 to 3 hrs.) at a temperature between 23° C. to 110° C. (preferably, at 20° C. to 40° C.). The finished supported catalyst is then isolated by filtration, rinsed with non-polar solvent (e.g., toluene, pentane), and dried.

4. If more than one metallocene is used, the metallocene precursors can be dissolved together with solvent to create one solution, or each metallocene can be dissolved individually.

5. The metallocene precursor(s) can be added to silica/alumoxane support/activator slurry together in one solution, or individual solutions of each metallocene precursor can be added in any order/sequence. In a preferred embodiment of the invention, multiple metallocene precursor(s) are added to silica/alumoxane support/activator slurry together in one solution.

Polymerization Processes

In embodiments herein, the invention relates to polymerization processes where monomer (such as propylene), and optionally comonomer, are contacted with a catalyst system comprising an activator and at least one metallocene compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof. In a preferred embodiment of the invention, the monomer comprises propylene and an optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and an optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment, one or more dienes are present in the polymer produced herein at up to 10 wt %, preferably at 0.00001 to 1.0 wt %, preferably 0.002 to 0.5 wt %, even more preferably 0.003 to 0.2 wt %, based upon the total weight of the composition. In some embodiments, 500 ppm or less of diene is added to the polymerization, preferably 400 ppm or less, preferably or 300 ppm or less. In other embodiments, at least 50 ppm of diene is added to the polymerization, or 100 ppm or more, or 150 ppm or more.

Preferred diolefin monomers useful in this invention include any hydrocarbon structure, preferably C4 to C30, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., di-vinyl monomers). More preferably, the diolefin monomers are linear di-vinyl monomers, most preferably, those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein, the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In some embodiments hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally scavengers (such as trialkyl aluminum compounds) are absent (e.g., present at zero mol %, alternately the scavenger is present at a molar ratio of scavenger metal to transition metal of less than 100:1, preferably less than 50:1, preferably less than 15:1, preferably less than 10:1); and 8) optionally, hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example, a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, pentyl, hexyl, octyl or an isomer thereof) or a combination thereof, such as diethyl zinc, methylalumoxane, trimethylaluminum, triisobutylaluminum, trioctylaluminum, or a combination thereof.

Polyolefin Products

This invention also relates to compositions of matter produced by the methods described herein.

In a preferred embodiment, the process described herein produces $C_2$ to $C_{20}$ olefin homopolymers or copolymers, such as ethylene-hexene, propylene-ethylene and/or propylene-alphaolefin (preferably $C_3$ to $C_{20}$) copolymers (such as propylene-hexene copolymers or propylene-octene copolymers) having low comonomer incorporation (such as low C6 wt %) and/or broad molecular weight distribution (MWD).

Likewise, the process of this invention produces olefin polymers, preferably polyethylene and polypropylene homopolymers and copolymers. In a preferred embodiment, the polymers produced herein are homopolymers of ethylene or copolymers of ethylene preferably having from 0 to 25 mol % (alternately from 0.5 to 20 mol %, alternately from 1 to 15 mol %, preferably from 3 to 10 mol %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene).

In a preferred embodiment, the polymers produced herein are homopolymers of propylene or are copolymers of propylene preferably having from 0 to 25 mol % (alternately from 0.5 to 20 mol %, alternately from 1 to 15 mol %, preferably from 3 to 10 mol %) of one or more of $C_2$ or $C_4$ to $C_{20}$ olefin comonomer (preferably ethylene or $C_4$ to $C_{12}$ alpha-olefin, preferably ethylene, butene, hexene, octene, decene, dodecene, preferably ethylene, butene, hexene, octene).

In a preferred embodiment, the monomer is ethylene and the comonomer is hexene, preferably from 0.5 to 15 mol % hexene, alternately 1 to 10 mol %.

Typically, the polymers produced herein have an Mw of 20,000 to 1,000,000 g/mol (preferably 60,000 to 300,000 g/mol), and/or an Mw/Mn of greater than 1 to 40 (alternately 1.2 to 20, alternately 1.3 to 10, alternately 1.4 to 8, alternately 1.5 to 6, alternately 2 to 6).

In a preferred embodiment, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Molecular weight and measurement methods are described in the Experimental Section, in the event of conflict between the "Rapid GPC" and the GPC-3D methods, the GPC-3D method shall control.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing polyethylenes or blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxial orientation can be accomplished using typical cold drawing or hot drawing methods. Biaxial orientation can be accomplished using tenter frame equipment or a double bubble process and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

In the following numbered paragraphs further embodiments are provided.

1. In a first embodiment, a catalyst compound represented by the formula:

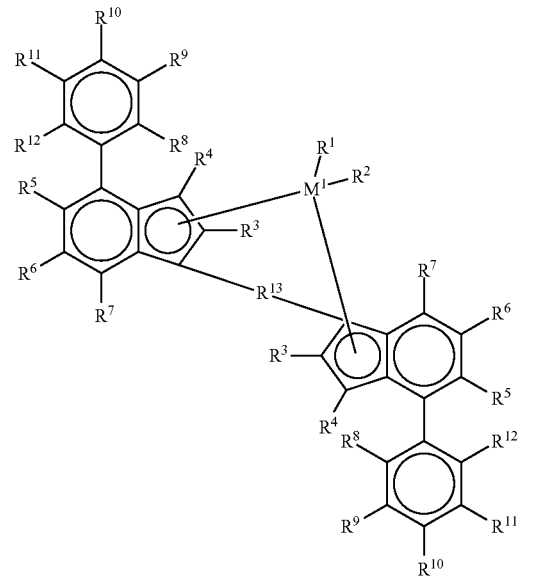

(I)

wherein $M^1$ is selected from the group consisting of titanium, zirconium, hafnium;

each $R^1$ and $R^2$ are identical or different and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ (preferably $C_8$-$C_{30}$) arylalkenyl group, an OH group or a halogen atom, or a conjugated diene which is optionally substituted with one or more hydrocarbyl, tri (hydrocarbyl) silyl groups or tri (hydrocarbyl) silylhydrocarbyl groups, said diene having up to 30 atoms not counting hydrogen;

each $R^3$ to $R^7$ are identical or different and are each a hydrogen atom, or a substituted or unsubstituted, branched or unbranched $C_1$-$C_{10}$ alkyl group;

$R^{13}$ is —$((R^{15*})_2Si$—$Si(R^{15})_2)$— wherein, each $R^{15}$ and $R^{15*}$ is identical or different and is a substituted or unsubstituted, branched or unbranched $C_1$-$C_{20}$ alkyl group, where preferably, each $R^{15}$ together do not form a ring, and/or each $R^{15*}$ together do not form a ring, and/or $R^{15}$ and $R^{15*}$ together do not form a ring;

each $R^8$, $R^{10}$ and $R^{12}$ are identical or different and are each a hydrogen atom or a substituted or unsubstituted, branched or unbranched $C_1$-$C_{10}$ alkyl group; and each $R^9$ and $R^{11}$ are identical or different and are a hydrogen atom or a substituted or unsubstituted, branched or unbranched $C_2$-$C_{20}$ alkyl group is presented.

2. The catalyst compound of paragraph 1, wherein $M^1$ is Hf or Zr.

3. The catalyst compound of paragraph 1 or 2, wherein each $R^3$ is a hydrogen atom and $R^8$ through $R^{12}$ are each hydrogen atoms.

4. The catalyst compound of paragraph 1 or 2, wherein each $R^3$ is a hydrogen atom or a $C_1$-$C_{10}$ alkyl group, $R^8$, $R^{10}$ and $R^{12}$ are each hydrogen atoms and each $R^9$ and $R^{11}$ are identical or different and are each a $C_3$-$C_{20}$ alkyl group.

5. The catalyst compound of paragraph 4, wherein each $R^3$ is a hydrogen atom and each $R^9$ and $R^{11}$ are each t-butyl groups.

6. The catalyst compound of any of paragraphs 1 through 5, wherein the rac/meso ratio of the catalyst compound is from 100/1 to 1/100.

7. The catalyst compound of any of paragraphs 1 through 6, wherein the catalyst compound is supported.

8. The catalyst compound of paragraph 7, wherein the support is silica.

9. A catalyst system comprising activator and the catalyst compound of any of paragraphs 1 to 8.

10. A process to polymerize ethylene comprising contacting ethylene and, optionally, one or more olefin comonomers, with the catalyst compound of any of paragraphs 1-8 or catalyst system of paragraph 9; wherein the polymer produced has at least 50 mol % ethylene and an $M_w$ between 20,000 g/mol and 400,000 g/mol.

11. The process of paragraph 10, wherein the rac and meso forms of the catalyst are not separated.

12. The process of either paragraphs 10 or 11, wherein the comonomers comprise one or more of propylene, butene, pentene, hexene, heptene, octene, nonene, decene, undecene, dodecene and isomers thereof.

13. The process of any of paragraphs 10 through 12, wherein the polymer has a PDI greater than 4, and has a g'vis of 0.95 or more.

14. The process of any of paragraphs 10 or 12, wherein the process occurs at a temperature of from about 0° C. to about 300° C., at a pressure in the range of from about 0.35 MPa to about 10 MPa, and at a time up to 300 minutes.

15. The process of any of paragraphs 9 through 14, wherein the activator comprises alumoxane.

16. The process of any of paragraphs 9 through 14, wherein the activator comprises a non-coordinating anion activator.

17. The process of paragraph 16, wherein activator is represented by the formula:

(Z)d+(Ad−)

wherein Z is (L-H) or a reducible Lewis Acid, L is a neutral Lewis base; H is hydrogen; (L-H)+ is a Bronsted acid; Ad− is a non-coordinating anion having the charge d−; and d is an integer from 1 to 3.

18. The process of paragraph 16, wherein activator is represented by the formula:

(Z)d+(Ad−)

wherein Ad− is a non-coordinating anion having the charge d−; d is an integer from 1 to 3, and Z is a reducible Lewis acid represented by the formula: (Ar3C+), where Ar is aryl or aryl substituted with a heteroatom, a $C_1$ to $C_{40}$ hydrocarbyl, or a substituted $C_1$ to $C_{40}$ hydrocarbyl.

19. The process of paragraph 18, wherein the activator is one or more of: N,N-dimethylanilinium tetrakis(pentafluorophenyl)borate, triphenylcarbenium tetrakis(pentafluorophenyl) borate, trimethylammonium tetrakis(perfluoronaphthyl)borate, triethylammonium tetrakis(perfluoronaphthyl)borate, tripropylammonium tetrakis(perfluoronaphthyl)borate, tri (n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, or N,N-diethylanilinium tetrakis(perfluoronaphthyl)borate.

20. The process of paragraph 10, wherein the polymer comprises less than 15% of comonomer, based upon the weight of the polymer, and the polymer has an $M_w$ of at 190,000 g/mol or more.

21. The process of paragraph 13, wherein the meso form of the catalyst or meso/rac mixtures provide a polymer with a PDI greater than 4.

22. The process of paragraph 13, wherein the rac form of the catalyst provides a polymer with a PDI of 2 to 3.

23. The catalyst compound of any of paragraphs 1 to 8, catalyst system of paragraph 9 or any of the processes of paragraphs 10 to 22, wherein each $R^{15}$ together do not form a ring and each $R^{15*}$ together do not form a ring.

24. The catalyst compound of any of paragraphs 1 to 8, catalyst system of paragraph 9 or any of the processes of paragraphs 10 to 22, wherein each $R^{15}$ together do not form a ring.

25. The catalyst compound of any of paragraphs 1 to 8 or paragraph 23, catalyst system of paragraph 9, or any of the processes of paragraphs 10 to 22, wherein $R^{15}$ and $R^{15*}$ together do not form a ring.

Experimental

D948, also referred to as Davison 948, is Silica SYLOPOL™ 948, available from WR Grace and Company, Columbia, Md., USA.

Catalyst 1 is D948 supported meso-tetramethyldisilylene bis(4-(3',5'-di-tert-butylphenyl)-indenyl) zirconium dichloride using procedure A.

Catalyst 2 is a supported catalyst made in a manner analogous to that described in U.S. Pat. No. 6,180,736 using the (1-Me-3-"BuCp)$_2$ZrCl$_2$ metallocene.

Catalyst 3 is D948 supported rac-dimethylsilylbis (2-methyl-4-phenyl indenyl) ZrCl$_2$ using procedure A.

Catalyst 4 is D948 supported rac-dimethylsilyl bis(2-cyclopropyl-4-(3',5'-di-tert-butylphenyl)-indenyl) ZrCl$_2$ using procedure A.

Catalyst 5 is F-D948 supported (1-Me-3-"BuCp)$_2$ZrCl$_2$ metallocene using procedure B.

Catalyst 6 is F-D948 supported meso-O(Me$_2$SiInd)$_2$ZrCl$_2$ (Ind=indenyl) using procedure B.

Catalyst 7 is F-D948 supported rac-Me$_2$Si(bistetrahydroindenyl)ZrCl$_2$ using procedure B.

Catalyst 8 is F-D948 supported rac-tetramethyldisilylene bis(4-(3',5'-di-tert-butylphenyl)-indenyl) zirconium dichloride using procedure B.

Catalyst 9 is F-D948 supported meso-tetramethyldisilylene bis(4-(3',5'-di-tert-butylphenyl)-indenyl) zirconium dichloride using procedure B.

Catalyst 10 is D948 supported meso-tetramethyldisilylene bis(4-(3',5'-di-tert-butylphenyl)-indenyl) zirconium dichloride using procedure C.

Catalyst 11 is D948 supported rac-tetramethyldisilylene bis(4-(3',5'-di-tert-butylphenyl)-indenyl) zirconium dichloride using procedure C.

Catalyst 12 is D948 supported rac/meso (1:1)-tetramethyldisilylene bis(4-(3',5'-di-tert-butylphenyl)-indenyl) zirconium dichloride using procedure C.

Catalyst 13 is D948 supported meso-tetramethyldisilylene bis(indenyl) zirconium dichloride using procedure C.

Catalyst 14 is D948 supported rac-tetramethyldisilylene bis(indenyl) zirconium dichloride using procedure C.

EXAMPLES

Synthesis of Tetramethyldisilylene bis(4-(3',5'-di-tert-butylphenyl)-indenyl) Zirconium Dichloride

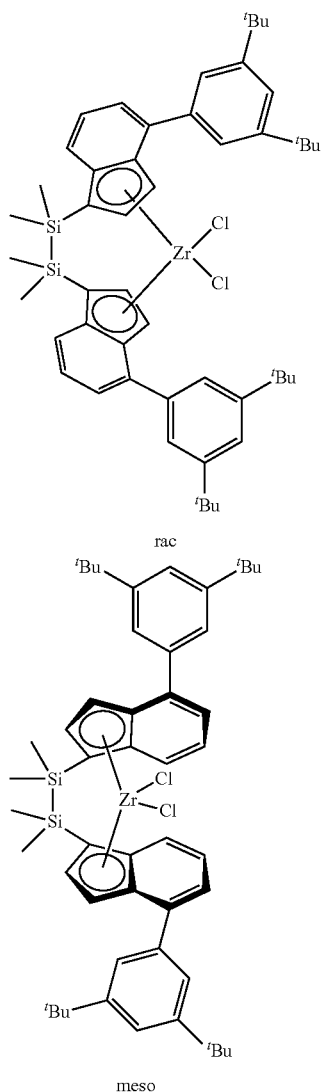

rac meso

Lithium {1-[4-(3',5'-di-tert-butylphenyl indenide]}

A solution of 7-(3,5-di-tert-butylphenyl)-indene (13.304 g, 43.76 mmol) in diethyl ether (100 mL) was precooled at −30° C. $^n$BuLi (2.5 M, 18.4 mL, 45.95 mmol) was added. The solution was stirred at room temperature for 3 hrs. All volatiles were evaporated. The residue was washed with cold pentane (30 mL) and dried under vacuum to give the crude product (13.28 g, 97%).

1,2-Bis(4-(3',5'-di-tert-butylphenyl)-1H-inden-1-yl)-1,1,2,2-tetramethyldisilane A solution of lithium {1-[4-(3,5-di-tert-butylphenyl indenide]} (13.25 g, 42.76 mmol) in diethyl ether (100 mL) was precooled to −30° C., then was treated with a solution of 1,2-dichloro-1,1,2,2-tetramethyldisilane (3.97 g, 21.38 mmol) in diethyl ether (30 mL), and the white slurry was stirred for 2 hours at room temperature. All volatiles were evaporated. The residue was extracted with hexane (50 mL) and toluene (100 mL), the combined extracts were washed with hexane (50 mL), then dried over vacuum to get the product as off-white solid (8.14 g, 53%).

Dilithium 1,1,2,2-tetramethyldisilyl bis(4-(3',5'-di-tert-butylphenyl)-1H-indenide)

A solution of 1,2-bis(4-(3,5-di-tert-butylphenyl)-1H-inden-1-yl)-1,1,2,2-tetramethyldisilane (8.13 g, 11.2 mmol) in diethyl ether (100 mL) was precooled to −30° C., then was treated with $^n$BuLi (2.5 M, 9.2 mL, 23.05 mmol). The solution was stirred at room temperature for 2 hrs. All volatiles were evaporated. The residue was washed with pentane (30 mL) and dried under vacuum to give the dilithium compound (8.26 g, 99%).

Tetramethyldisilylene bis(4-(3',5'-di-tert-butylphenyl)-indenyl) Zirconium Dichloride A precooled solution of the dilithium 1,1,2,2-tetramethyldisilyl bis(4-(3,5-di-tert-butylphenyl)-1H-indenide) (8.26 g, 11.2 mmol) in toluene (50 mL) was treated with ZrCl$_4$ (2.58 g, 11.2 mmol). The reaction was stirred at room temperature for 3 hours. The mixture was filtered through Celite®, and the filtrate was concentrated to dryness to get a crude product (9.72 g) with rac/meso ratio of 1.4:1. The crude product was recrystallized from 50 mL of hexane, filtered at 45° C. to give 1.07 g (yield 10.8%) of rac-metallocene with rac/meso ratio of 35:1. The filtrate was cooled down gradually and filtered at room temperature to get 1.58 g (yield 16%) of meso-metallocene with meso/rac ratio of 46:1. $^1$H NMR (400 MHz, C$_6$D$_6$, 23° C.), rac-isomer: δ 7.70 (d, 4H), 7.60 (d, 2H), 7.55 (dd, 2H), 7.22 (dd, 2H), 7.09 (s, 1H), 7.07 (s, 1H), 6.88 (dd, 2H), 6.53 (d, 2H), 1.33 (s, $^t$Bu×4, 36H), 0.56 (s, SiMe×2, 6H), 0.45 (s, SiMe×2, 6H); meso-isomer: δ 7.73 (d, 4H), 7.57 (dd, 2H), 7.52 (dd, 2H), 7.19 (dd, 2H), 7.10 (s, 1H), 7.08 (s, 1H), 7.00 (dd, 2H), 6.31 (d, 2H), 1.37 (s, $^t$Bu×4, 36H), 0.62 (s, SiMe×2, 6H), 0.40 (s, SiMe×2, 6H).

Synthesis of Tetramethyldisilylene Bis(indenyl) Zirconium Dichloride

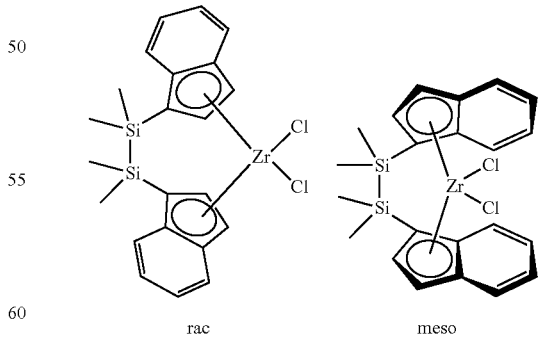

rac                    meso

Lithium Indenide

A solution of 1H-indene (5.0 g, 43 mmol) in diethyl ether (50 mL) was treated with nBuLi (2.5 M, 17.2 mL, 45 mmol)

at −35° C., and the solution was stirred at room temperature for 3 hrs. All volatiles were evaporated. The residue was washed with cool pentane (2×10 mL) and dried under vacuum to give a white solid as product (4.261 g).

1,2-di(1H-inden-1-yl)-1,1,2,2-tetramethyldisilane

A solution of lithium indenide (4.2 g, 34.4 mmol) in diethyl ether (50 mL) was treated with 1,2-dichloro-1,1,2,2-tetramethyldisilane (3.2 g, 17.2 mmol) at −35° C., and the resulting white slurry was stirred at room temperature for 3 hrs. Then all volatiles were evaporated. The residue was extracted with mixed solvents (15 mL of hexane and 5 mL of toluene) twice. The filtrate was concentrated to dryness and dried under vacuum to give a white solid (5.626 g).

Dilithium Tetramethyldisilyl-indenide

A solution of the 1,2-di(1H-inden-1-yl)-1,1,2,2-tetramethyldisilane (5.57 g, 16.1 mmol) in diethyl ether (50 mL) was treated with nBuLi (2.5 M, 13.2 mL, 33 mmol). The mixture was stirred at room temperature for 3 hrs. Then the solvents were evaporated, the residue was washed with hexane (2×20 mL) and dried under vacuum to give a white solid as the dilithium compound (4.419 g).

Tetramethyldisilylene-bisindenyl Zirconium Dichloride

A precooled suspension of dilithium tetramethyldisilyl-indenide (4.3 g, 12.0 mmol) in Et$_2$O (50 mL) was treated with a powder of ZrCl$_4$ (2.76 g, 12.0 mmol). The mixture was stirred at room temperature overnight. The solvent was evaporated to dryness. The residue was extracted with mixed solvents (15 mL of hexane and 5 mL of toluene) for twice. The filtrates were evaporated to dryness and recrystallized (10 mL of toluene and 20 mL of hexane, refluxed to room temperature) to afford 0.210 g (3.5%) of the meso-isomer with a rac/meso-ratio=1:100. The combined filtrate was concentrated and recrystallized (5 mL of toluene and 30 mL of hexane, refluxed to room temperature) to afford 0.118 g (2%) of the rac-isomer with a rac/meso-ratio=67:1. $^1$HNMR (CDCl$_3$, 400 MHz, 23° C.), meso-isomer: 7.66 (dt, 2H), 7.46 (dd, 2H), 7.30-7.12 (m, 4H), 6.96 (d, 2H), 6.68 (dd, 2H), 0.72 (s, 6H), 0.65 (s, 6H), rac-isomer: 7.81 (dd, 2H), 7.69 (dt, 2H), 7.41-7.20 (m, 4H), 6.63 (d, 2H), 6.26 (dd, 2H), 0.73 (s, 6H), 0.63 (s, 6H).

Preparation of Supported Catalysts on D948 Using Method A

Representative Procedure for Preparation of 130° C. 948 SMAO

130° C. Calcined Davison 948 Silica (20.8606 g, calcined at 130° C.) was slurried in 121 mL of toluene and chilled in the freezer (−35° C.). MAO (50.5542 g of a 30% wt solution in toluene) was added slowly in 3 parts with the silica slurry returned to the freezer for a few minutes (approx. 2 min) between additions. The slurry was stirred at room temperature for 2 hrs., filtered with a fine glass frit filter, reslurried in 80 mL of toluene for 15 min at room temperature, and then filtered again. The solid was reslurried in 80 mL of toluene at 80° C. for 30 min and then filtered. The solid was reslurried in 80 mL of toluene at 80° C. for 30 min and then filtered a final time. The celstir and solid were washed out with 40 mL of toluene. The solid was then washed with pentane and dried under vacuum for 24 hours. Collected 28.9406 g of a free flowing white powder.

Representative Example for Preparation of Catalyst 1 meso-tetramethyldisilylene bis(4-(3',5'-di-tert-butylphenyl)-indenyl) zirconium dichloride (18.4 mg, 0.0208 mmol) was combined with MAO (0.1726 g of a 30% by weight toluene solution) and 2 mL of toluene and stirred for 1 hr. 130° C. 948 SMAO (0.5214 g) was slurried in 20 mL of toluene and chilled to −35° C. The catalyst solution was added to the slurry and the slurry was then stirred for 1 hr. with occasional chilling. The slurry was then stirred at 40° C. for 1 hr. The slurry was filtered, reslurried in 20 mL of toluene for 30 min at 60° C. and refiltered. The solid was reslurried at 60° C. twice more. After the final filtration the celstir was washed out with 20 mL of toluene and added to the solid on the frit. The solid was dried under vacuum overnight to give 0.4503 g of tan solid.

Representative Example for Preparation of Catalyst 3

In a 20 mL rac-dimethylsilyl bis(2-methyl-4-phenyl-indenyl) zirconium dichloride (23.3 mg, 0.0396 mmol) was stirred alongside MAO (30% by weight in toluene, 0.3278 g of solution) along with another 2 mL of toluene for 1 hr. In a small celstir 130° C. SMAO (0.9915 g) was slurried in 20 mL of toluene. The catalyst solution was added to the slurry. The slurry stirred for 1 hr. The slurry was then filtered using a fine glass frit, washed four times with 20 mL of toluene, and the red solid was dried under vacuum. Collected 0.9639 g of red solid.

Representative Example for Preparation of Catalyst 4

In a 20 mL vial rac-dimethylsilyl bis(2-cyclopropyl-4-(3', 5'-di-tert-butylphenyl)-indenyl) zirconium dichloride (25.2 mg, 0.0278 mmol) was stirred alongside MAO (30% by weight in toluene, 0.2345 g of solution) along with another 2 mL of toluene for 1 hr. In a small celstir 130° C. calcined silica pretreated with MAO (130° C. SMAO) (0.6954 g) was slurried in 20 mL of toluene. The celstir was chilled for 1 min in the freezer (−35° C.) before the catalyst solution was added to the slurry. The slurry was stirred for 1 hr. while spending 1 min of every 10 min in the freezer. The slurry was then heated to 40° C. and stirred for 2 hrs. The slurry was filtered using a fine glass frit, and then reslurried in 20 mL of toluene and stirred for an additional 30 min at 60° C. The slurry was filtered again, and then reslurried in 20 mL of toluene and stirred for an additional 30 min at 60° C. The slurry was filtered, and then reslurried in 20 mL of toluene and stirred for an additional 30 min at 60° C. and then filtered for the final time. The celstir was washed out with 20 mL of toluene and the solid was dried under vacuum. Collected 0.619 g of pink solid.

Preparation of Supported Catalysts on Fluoridated D948 silica (F-D948) Using Method B Preparation of Fluoridated D948 Silica (F-D948)

1.18 g (NH$_4$)$_2$SiF$_6$ was dissolved in 7.00 g water in a 20 mL glass vial. 50 g of Grace Davison D948™ silica and 200 g of toluene were combined in a 250 mL Wheaton CEL- STIR™. Under vigorous stirring, the aqueous stock solution of (NH$_4$)$_2$SiF$_6$ was added via a syringe to the toluene slurry of silica. The mixture was allowed to stir at room temperature for 2.5 hrs. The slurry was filtered through a 110 mL Optichem™ disposable polyethylene frit, rinsed with 200 g pentane three times, then dried in air overnight to yield a white, free-flowing solid. The solid was transferred into a tube furnace, and was heated under constant nitrogen flow (temperature program: 25° C./h ramped to 150° C.; held at 150° C. for 4 hrs.; 50° C./h ramped to 200° C.; held at 200° C. for 4 hrs.; cooled down to room temperature). 46 g of F-silica was collected after the calcination. The calculated "F" loading was 0.9 mmol/g.

Preparation of Supported Methylalumoxane from Fluoridated D948 Silica (sMAO-F-D948)

In a drybox, 34.5 g MAO toluene solution (Albermarle, 13.6 wt % Al) and 100 g of anhydrous toluene were combined in a 250 mL Wheaton CELSTIR™. The stir rate was set to 450 rpm. Every 5 min, 5 g of F-D948 silica was slowly added to the Celstir. A total amount of 27.6 g of F-D948 silica was added over a period of 30 min. The resulting slurry was allowed to stir at room temperature for 15 min. Then the Celstir was placed in a sand bath heated to 100° C. The slurry was heated at 100° C. for an additional 3 hrs. at a stirring rate of 215 rpm. The final slurry was filtered through a 110 mL Optichem disposable polyethylene frit. The solid collected in the frit was first rinsed with 80 g toluene for 2 times, then 60 g pentane for 3 times. The solid was dried in-vacuo for 12 hrs. 37.4 g of free-flowing sMAO-F-D948 was obtained. The calculated Al loading was 4.4 mmol Al per gram of sMAO.

Representative Example for Catalyst 8

18.5 mg rac-tetramethyldisilylene bis(4-(3',5'-di-tert-butylphenyl)-indenyl) zirconium dichloride (20.9 μmol) is combined with 0.500 g sMAO-F-D948 in a 20 mL glass vial. 4.0 g toluene was then added to the glass vial. The glass vial is capped with a Teflon-lined cap and vortexed at room temperature for 90 min. The resulting slurry is filtered through a 18 mL polyethylene frit (10 micron), and rinsed with 3 g toluene for 3 times, followed by 2 g of pentane for 3 times. The collected solid is dried under vacuum for 40 min. Free-flowing yellow solid of is collected. Calculated catalyst loading: 42 μmol/g (catalyst loading=μmol of catalyst/gram of added sMAO).

Catalysts 5, 6, 7, and 9 were prepared by identical methodology.

Preparation of Supported Catalysts on D948 Using Method C

Representative Procedure for Preparation of 600° C. 948 SMAO

In a large celstir, 600° C. silica (45.6903 g) was slurried in 250 mL of toluene and heated to 80° C. to 100° C. MAO (79.2482 g of a 30% by weight solution) was added slowly to the slurry. Stir for 1 hr. NMR analysis shows excess MAO. The solid was filtered, washed three times with toluene and dried under vacuum for 2 days to give 68.1106 g of white solid.

Representative Example for Preparation of Catalyst 10 meso-tetramethyldisilylene bis(4-(3',5'-di-tert-butylphenyl)-indenyl) zirconium dichloride (19.0 mg, 0.0215 mmol) was dissolved in 3 mL of toluene. 600° C. 948 SMAO (0.5384 g) was slurried in 15 mL of toluene. The catalyst solution was added to the slurry; the catalyst vial was washed out with another 2 mL of toluene and added to the slurry. The slurry stirred for 1 h, was filtered, washed three times with 15 mL of toluene apiece, and washed twice with pentane. The solid is dried under vacuum to give 0.4672 g of yellow solid.

Representative Example for Preparation of Catalyst 11 rac-tetramethyldisilylene bis(4-(3',5'-di-tert-butylphenyl)-indenyl) zirconium dichloride (22.7 mg, 0.0257 mmol) was dissolved in 5 mL of toluene. 600° C. 948 SMAO (0.6424 g) was slurried in 15 mL of toluene. The catalyst solution was added to the slurry. The slurry was stirred for 85 min, was filtered, washed three times with 15 mL of toluene apiece, and washed twice with pentane. The solid is dried under vacuum to give 0.604 g of yellow solid.

Representative Example for Preparation of Catalyst 12 rac-tetramethyldisilylene bis(4-(3',5'-di-tert-butylphenyl)-indenyl) zirconium dichloride (18.9 mg, 0.0214 mmol) and meso-tetramethyldisilylene bis(4-(3',5'-di-tert-butylphenyl)-indenyl) zirconium dichloride (18.9 mg, 0.0214 mmol) were dissolved together in 5 mL of toluene. 600° C. calcined 948 SMAO (1.0705 g) was slurried in 15 mL of toluene. The catalyst solution was added to the slurry. The slurry was stirred for 1 hr. before being filtered, washed three times with 15 mL of toluene, and washed twice with pentane. The solid was dried under vacuum to give 1.0013 g of a yellow/orange solid.

Representative Example for Preparation of Catalyst 13

600° C. 948 SMAO (0.8686 g) was slurried in 15 mL of toluene. Meso-tetramethyldisilylene bis(indenyl) zirconium dichloride (17.5 mg, 0.0345 mmol) was dissolved in 5 mL of toluene and added to the slurry. The slurry was stirred for 1 hr. and then filtered, washed three times with 15 mL of toluene each, and then washed twice with pentane. The solid was dried under vacuum to give 0.7986 g of yellow powder.

Representative Example for Preparation of Catalyst 14

600° C. 948 SMAO (1.0109 g) was slurried in 15 mL of toluene. Rac-tetramethyldisilylene bis(indenyl) zirconium dichloride (20.4 mg, 0.0403 mmol) was dissolved in 5 mL of toluene and added to the slurry. The slurry was stirred for 1 hr. and then filtered, washed three times with 15 mL of toluene each, and then washed twice with pentane. The solid was dried under vacuum to give 0.9826 g of yellow powder.

General Procedure for High Throughput Ethylene/1-hexene Polymerization and Polymer Characterization (Table 1 and Table 2)

Unless stated otherwise ethylene homopolymerization and ethylene-hexene copolymerizations are carried out in a parallel pressure reactor, as generally described in U.S. Pat. No. 6,306,658; U.S. Pat. No. 6,455,316; WO 00/09255; and Murphy et al., J. Am. Chem. Soc., 2003, Vol. 125, pp.

4306-4317, each of which is incorporated by reference herein in its entirety. Although specific quantities, temperatures, solvents, reactants, reactants ratios, pressures, and other variables may need to be adjusted from one reaction to the next, the following describes a typical polymerization performed in a parallel, pressure reactor.

Preparation of catalyst slurry for high throughput run:

In a dry box, 45 mg of supported catalyst is weighed into a 20 mL glass vial. 15 mL of toluene is added to the vial to make a slurry that contained 3 mg supported catalyst/mL slurry. The resulting mixture is vortexed prior to injection.

Starting material preparations:

Solvents, polymerization grade toluene and isohexane are supplied by ExxonMobil Chemical Company and thoroughly dried and degassed prior to use. Polymerization grade ethylene is used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

TnOAl (tri-n-octylaluminum, neat) is used as a 2 mmol/L solution in toluene.

Polymerizations are conducted in an inert atmosphere ($N_2$) drybox using autoclaves equipped with an external heater for temperature control, glass inserts (internal volume of reactor=22.5 mL), septum inlets, regulated supply of nitrogen, ethylene and hexene, and equipped with disposable PEEK mechanical stirrers (800 RPM). The autoclaves are prepared by purging with dry nitrogen prior to use.

Ethylene/1-hexene Copolymerization

The reactor is prepared as described above, and then purged with ethylene. Isohexane, 1-hexene and TnOAl are added via syringe at room temperature and atmospheric pressure. The reactor is then brought to process temperature (85° C.) and charged with ethylene to process pressure (130 psig=896 kPa) while stirring at 800 RPM. The transition metal compound "TMC" (100 µL of a 3 mg/mL toluene slurry, unless indicated otherwise) is added via syringe with the reactor at process conditions. TnOAl is used as 200 µL of a 20 mmol/L in isohexane solution. Amounts of reagents not specified above are given in Table 1. No other reagent is used. Ethylene is allowed to enter (through the use of computer controlled solenoid valves) the autoclaves during polymerization to maintain reactor gauge pressure (+/−2 psig). Reactor temperature is monitored and typically maintained within +/−1° C. Polymerizations are halted by addition of approximately 50 psi O2/Ar (5 mol % O2) gas mixture to the autoclaves for approximately 30 seconds. The polymerizations are quenched after a predetermined cumulative amount of ethylene had been added or for a maximum of 45 minutes polymerization time. In addition to the quench time for each run, the reactors are cooled and vented. The polymer is isolated after the solvent is removed in-vacuo. Yields reported include total weight of polymer and residual catalyst. The resultant polymer is analyzed by Rapid GPC to determine the molecular weight and by DSC to determine the melting point.

To determine various molecular weight related values of the high throughput samples by GPC, high temperature size exclusion chromatography was performed using an automated "Rapid GPC" system. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using a Polymer Char IR4 detector. The molecular weights presented are relative to linear polystyrene standards and are uncorrected.

The amount of hexene incorporated in the polymers (wt %) was determined by rapid FT-IR spectroscopy on a Bruker Vertex 70 IR in reflection mode. Samples were prepared in a thin film format by evaporative deposition techniques. Weight percent hexene was obtained from the ratio of peak heights in the ranges of 1377-1382 $cm^{-1}$ to 4300-4340 $cm^{-1}$. This method was calibrated using a set of ethylene hexene copolymers with a range of known wt % hexene content.

Differential Scanning Calorimetry (DSC) measurements were performed on a TA-Q200 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

General Procedure for Polymerization in 2 L Reactor

A 2 L autoclave reactor was baked out at 100° C. for at least 1 hr. The reactor was cooled to room temperature. 2 mL of a 0.091M TNOAL solution in hexane was loaded into a catalyst tube as a scavenger and injected into the reactor with nitrogen gas. The nitrogen in the reactor was vented down until the pressure was just above ambient pressure. 600 mL of isohexane was added to the reactor. The reactor was heated to 85° C. and the stir rate was set to 500 rpm. When the proper temperature had been reached 20 psi of ethylene was added to the reactor. A second cat tube containing the catalyst and 2 mL of pentane was then attached to the reactor. The catalyst was pushed into the reactor with 200 mL of isohexane. A constant ethylene pressure, approximately 130 psi on top of the pressure of isohexane, approximately 190 psi total, was bubbled through the cat tube and the reactors dip tube. The reactor stirred for 30 min before being vented and cooled down. The polymer was collected in a beaker and placed under air purge to evaporate the isohexane and collect the dry polymer.

Ethylene-Hexene Copolymerization

A 2 L autoclave reactor is baked out at 100° C. for at least 1 hr. The reactor is cooled to room temperature. 2 mL of a 0.091M TNOAL solution in hexane is loaded into a catalyst tube as a scavenger and injected into the reactor with nitrogen gas. The nitrogen in the reactor is vented down until the pressure is just above ambient pressure. 300 mL of isohexane is added to the reactor. A second catalyst tube containing 1-hexene is then attached to the reactor. The 1-hexene is injected with an additional 300 mL of isohexane. The reactor is heated to 85° C. and the stir rate is set to 500 rpm. When the proper temperature has been reached 20 psi of ethylene is added to the reactor. A third cat tube containing the catalyst and 2 mL of pentane is then attached to the reactor. The catalyst is pushed into the reactor with 200 mL of isohexane. A constant ethylene pressure, approximately 130 psi on top of the pressure of isohexane, approximately 190-200 psi total, is bubbled through the cat tube and the reactors dip tube. The reactor stirs for 30 min before being vented and cooled down. The polymer is collected in a beaker and placed under air or nitrogen purge to evaporate the isohexane and collect the dry polymer.

Room Temperature (RT) is 25° C. unless otherwise indicated.

Products were characterized as follows:

$^1$H NMR $^1$H NMR data was collected at room temperature in a 5 mm probe using a Varian spectrometer with a $^1$H frequency of at least 400 MHz. Data was recorded using a maximum pulse width of 45° C., 8 seconds between pulses and signal averaging 120 transients.

Gel Permeation Chromatography with Three Detectors (GPC-3D) (Used Here for Polymers Produced in the 2 Liter Reactor)

Mw, Mn and Mw/Mn are determined by using a High Temperature Gel Permeation Chromatography (Agilent PL-220), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, 2001, Vol. 34(19), pp. 6812-6820, and references therein. Three Agilent PLgel 10 µm Mixed-B LS columns are used. The nominal flow rate is 0.5 mL/min, and the nominal injection volume is 300 µL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1,2,4-trichlorobenzene (TCB). The TCB mixture is then filtered through a 0.1 µm Teflon filter. The TCB is then degassed with an online degasser before entering the GPC-3D. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/mL at room temperature and 1.284 g/mL at 145° C. The injection concentration is from 0.5 to 2.0 mg/mL, with lower concentrations being used for higher molecular weight samples. Prior to running each sample the DRI detector and the viscometer are purged. Flow rate in the apparatus is then increased to 0.5 mL/minute, and the DRI is allowed to stabilize for 8 hours before injecting the first sample. The LS laser is turned on at least 1 to 1.5 hours before running the samples. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 145° C. and λ=690 nm. Units on parameters throughout this description of the GPC-3D method are such that concentration is expressed in g/cm$^3$, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, Light Scattering from Polymer Solutions, Academic Press, 1971):

$$\frac{K_o c}{\Delta R(\theta)} = \frac{1}{MP(\theta)} + 2A_2 c$$

Here, ΔR(θ) is the measured excess Rayleigh scattering intensity at scattering angle θ, c is the polymer concentration determined from the DRI analysis, $A_2$ is the second virial coefficient. P(θ) is the form factor for a monodisperse random coil, and $K_o$ is the optical constant for the system:

$$K_o = \frac{4\pi^2 n^2 \left(\frac{dn}{dc}\right)^2}{\lambda^4 N_A}$$

where $N_A$ is Avogadro's number, and (dn/dc) is the refractive index increment for the system, which take the same value as the one obtained from DRI method. The refractive index, n=1.500 for TCB at 145° C. and λ=657 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c is concentration and was determined from the DRI output.

The branching index ($g'_{vis}$) is calculated using the output of the GPC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'vis = \frac{[\eta]_{avg}}{k M_v^\alpha}$$

where, for purpose of this invention and claims thereto, α=0.695 for ethylene, propylene, and butene polymers; and k=0.000579 for ethylene polymers, k=0.000262 for propylene polymers, and k=0.000181 for butene polymers and $M_v$ is the viscosity-average molecular weight based on molecular weights determined by LS analysis. For ethylene copolymers, k decreases with increasing comonomer content. Z average branching index ($g'_{Zave}$) is calculated using Ci=polymer concentration in the slice i in the polymer peak times the mass of the slice squared, $Mi^2$.

Experimental and analysis details not described above, including how the detectors are calibrated and how to calculate the composition dependence of Mark-Houwink parameters and the second-virial coefficient, are described by T. Sun, P. Brant, R. R. Chance, and W. W. Graessley (*Macromolecules*, 2001, Vol. 34(19), pp. 6812-6820).

All molecular weights are weight average unless otherwise noted. All molecular weights are reported in g/mol unless otherwise noted.

C6 wt % is determined by $^1$H NMR.

Methyl groups per 1000 carbons (CH$_3$/1000 Carbons) is determined by $^1$H NMR.

Melt Index (MI, also referred to as I2) is measured according to ASTM D1238 at 190° C., under a load of 2.16 kg unless otherwise noted. The units for MI are g/10 min or dg/min.

High Load Melt Index (HLMI, also referred to as I21) is the melt flow rate measured according to ASTM D-1238 at 190° C., under a load of 21.6 kg. The units for HLMI are g/10 min or dg/min.

Melt Index Ratio (MIR) is the ratio of the high load melt index to the melt index, or I21/I2.

TABLE 1

Small Scale Ethylene 1-hexene Copolymerization Using Supported Catalysts. Conditions: 85° C.; catalyst, 0.3 mg; ethylene, 130 psi; isohexane solvent; total volume = 5 mL

| Run | Catalyst | 1-hexene (µmol) | Quench time (s) | Yield (g) | Mw g/mol | Mn g/mol | Mw/Mn | C6 wt % | Primary Tm (° C.) | Activity (g polymer/g) |
|---|---|---|---|---|---|---|---|---|---|---|
| 1 | Catalyst 1 | 0 | 2096 | 0.0811 | 789420 | 161157 | 4.9 | 0 | 135.5 | 465 |
| 2 |  | 200 | 1896 | 0.085 | 690700 | 150179 | 4.6 | 1.8 | 132.1 | 539 |
| 3 |  | 400 | 1618 | 0.0931 | 670236 | 140841 | 4.8 | 2.1 | 130.0 | 692 |
| 4 |  | 600 | 1314 | 0.0866 | 581041 | 124214 | 4.7 | 3.2 | 128.5 | 792 |
| 5 |  | 800 | 1266 | 0.0867 | 596106 | 153510 | 3.9 | 3.5 | 127.4 | 824 |
| 6 |  | 1000 | 1160 | 0.094 | 454816 | 124150 | 3.7 | 3.6 | 126.3 | 974 |
| 7 | Catalyst 2 | 0 | 2703 | 0.0547 | 518268 | 235030 | 2.2 | 0 | 135.4 | 243 |
| 8 |  | 200 | 1077 | 0.0917 | 481343 | 242969 | 2.0 | 2.2 | 129.0 | 1024 |
| 9 |  | 400 | 1124 | 0.0862 | 461974 | 210350 | 2.2 | 3.3 | 126.0 | 922 |
| 10 |  | 600 | 1002 | 0.0912 | 472875 | 243652 | 1.9 | 3.5 | 124.2 | 1094 |
| 11 |  | 800 | 924 | 0.0874 | 469786 | 230470 | 2.0 | 4.7 | 121.3 | 1138 |
| 12 |  | 1000 | 879 | 0.0865 | 497122 | 245544 | 2.0 | 5.0 | 120.1 | 1183 |
| 13 | Catalyst 3 | 0 | 883 | 0.0569 | 1173971 | 452162 | 2.6 | 0 | 132.2 | 775 |
| 14 |  | 200 | 167 | 0.1249 | 1198118 | 418363 | 2.9 | 7.5 | 113.9 | 8998 |
| 15 |  | 400 | 154 | 0.1233 | 927351 | 309263 | 3.0 | 11.6 | 104.6 | 9633 |
| 16 |  | 600 | 164 | 0.1241 | 854783 | 313397 | 2.7 | 14.5 | 97.5 | 9104 |
| 17 |  | 800 | 258 | 0.0974 | 820275 | 264286 | 3.1 | 18.9 | 90.3 | 4548 |
| 18 |  | 1000 | 302 | 0.1135 | 753956 | 260726 | 2.9 | 18.4 | 83.3 | 4513 |
| 19 | Catalyst 4 | 0 | 2702 | 0.0587 | 1406580 | 439160 | 3.2 | 0 | 133.3 | 261 |
| 20 |  | 400 | 539 | 0.1078 | 1295566 | 448089 | 2.9 | 11.5 | 100.5 | 2403 |
| 21 |  | 600 | 1121 | 0.1093 | 745956 | 308380 | 2.4 | 15.9 | 88.8 | 1172 |
| 22 |  | 800 | 1803 | 0.1017 | 591477 | 288102 | 2.1 | 18.4 | 77.2 | 678 |
| 23 |  | 1000 | 1522 | 0.1202 | 504905 | 237236 | 2.1 | 21.1 | 68.5 | 950 |

TABLE 2

Small Scale Ethylene 1-hexene Copolymerization Using F-D948 Supported Catalysts. Conditions: 85° C.; catalyst, 0.3 mg; ethylene, 130 psi; isohexane solvent; total volume = 5 mL

| | 6 mol % C6 in feed | | | 11 mol % C6 in feed | | |
|---|---|---|---|---|---|---|
| MCN | Activity (kg/mol*h) | Mw (kg/mol) | wt % C6 | Activity (kg/mol*h) | Mw (kg/mol) | wt % C6 |
| Catalyst 5 | 14224 | 478 | 2.5 | 21354 | 438 | 3.8 |
| Catalyst 6 | 11828 | 507 | 1.5 | | | |
| Catalyst 7 | 41962 | 507 | 3.9 | | | |
| Catalyst 8 | 15483 | 544 | 2.5 | 13831 | 540 | 3.4 |
| Catalyst 9 | 16734 | 517 | 2.5 | | | |

TABLE 3

Ethylene-Hexene Polymerization in 2 L Reactor using Catalysts Supported by Procedure C
Temp = 85° C.

| Run | Catalyst | Cat loading (mg) | Run time (min) | 1-hexene (mL) | Yield (g) | Activity (g polymer/g cat · h) | Activity (kg polymer/mol cat · h) | MI (dg/min) | MIR | CH$_3$/1000C | Mw (DRI) (kg/mol) | Mn (DRI) (kg/mol) | Mw/Mn |
|---|---|---|---|---|---|---|---|---|---|---|---|---|---|
| 1 | Catalyst 10 | 50.0 | 30 | 0 | 19.651 | 786 | 20364 | 0.056 | 47.55 | | 278 | 52 | 5.3 |
| 2 | Catalyst 10 | 46.4 | 20 | 10 | 18.799 | 1215 | 31488 | 0.077 | 63.60 | 2.4 | 197 | 48 | 4.2 |
| 3 | Catalyst 11 | 54.4 | 30 | 0 | 9.869 | 363 | 9400 | 0.045 | 27.13 | | 280 | 84 | 3.3 |
| 4 | Catalyst 11 | 46.0 | 30 | 10 | 8.140 | 354 | 9169 | 0.066 | 27.89 | 3.2 | 231 | 82 | 2.8 |
| 5 | Catalyst 12 | 51.0 | 30 | 0 | 17.611 | 691 | 17892 | 0.028 | 36.25 | | 292 | 72 | 4.1 |
| 6 | Catalyst 12 | 58.0 | 32 | 10 | 28.047 | 907 | 23489 | 0.045 | 41.87 | 2.0 | 271 | 56 | 4.8 |
| 7 | Catalyst 2 | 54.9 | 30 | 0 | 11.461 | 418 | 10438 | 0.036 | 54.03 | | | | |
| 8 | Catalyst 2 | 47.7 | 30 | 10 | 18.550 | 778 | 19444 | 0.245 | 18.91 | 3.1 | 158 | 60 | 2.6 |

TABLE 3-continued

Ethylene-Hexene Polymerization in 2 L Reactor using Catalysts Supported by Procedure C
Temp = 85° C.

| Run | Catalyst | Cat loading (mg) | Run time (min) | 1-hexene (mL) | Yield (g) | Activity (g polymer/ g cat · h) | Activity (kg polymer/ mol cat · h) | MI (dg/min) | MIR | CH$_3$/ 1000C | Mw (DRI) (kg/mol) | Mn (DRI) (kg/mol) | Mw/ Mn |
|---|---|---|---|---|---|---|---|---|---|---|---|---|---|
| 9 | Catalyst 13 | 52.3 | 30 | 0 | 18.035 | 690 | 17372 | 0.023 | 188.8 | | | | |
| 10 | Catalyst 13 | 57.3 | 30 | 10 | 27.821 | 971 | 24460 | 0.459 | 33.015 | | | | |
| 11 | Catalyst 13 | 60.5 | 30 | 10 | 54.371 | 1797 | 45274 | 0.236 | 30.665 | | | | |
| 12 | Catalyst 14 | 64.3 | 30 | 0 | 10.101 | 314 | 8035 | N/A (could not get MI) | | | | | |
| 13 | Catalyst 14 | 63.2 | 30 | 10 | 12.082 | 382 | 9779 | 0.079 | 22.949 | | | | |

Figure 2:
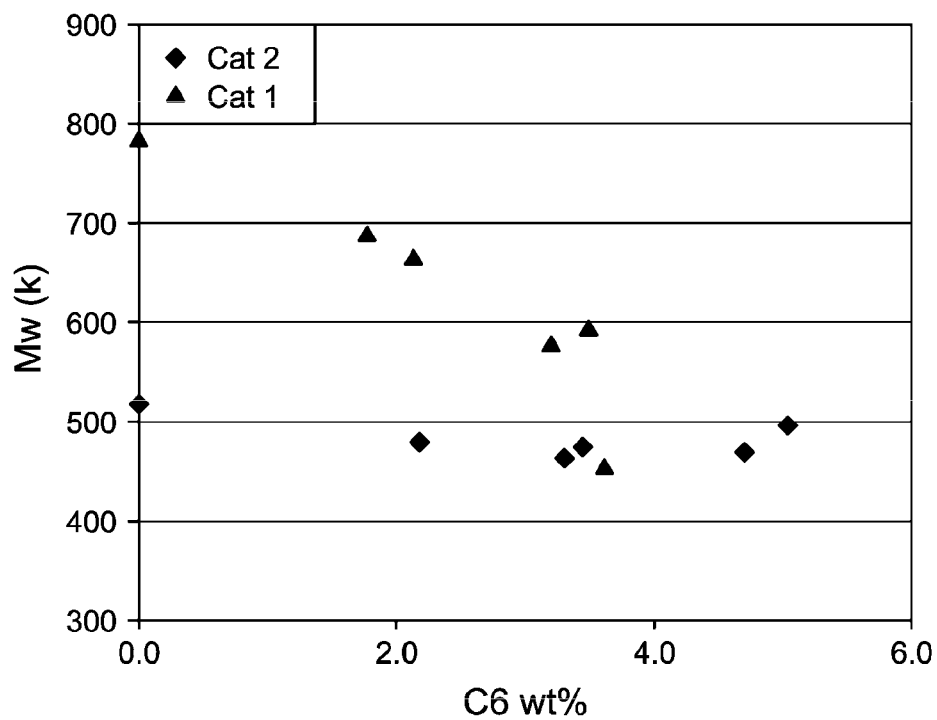
FIG. 2 is a representative plot of Mw vs 1-hexene Incorporation (C6 wt %) for Catalyst 1 in comparison to Catalyst 2 in Table 1.

As shown in Table 1 and FIG. 1, Catalyst 1 was shown to be the best poor comonomer incorporating catalyst among those tested under similar 1-hexene loading. In addition, as seen from FIG. 2, Catalyst 1 has higher Mw capabilities than another poor comonomer incorporating Catalyst 2 under similar C6 wt % incorporation conditions.

Figure 3:
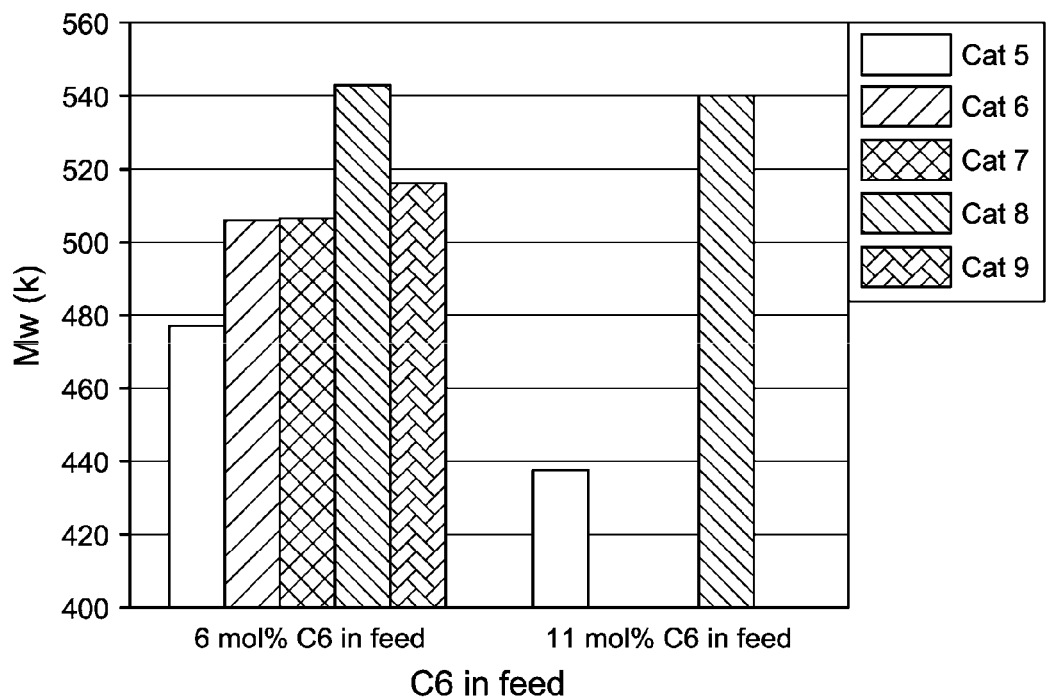
FIG. 3 is a representative plot of Mw (k) vs 1-hexene in feed for Poor Comonomer Incorporating Catalysts in Table 2.
Figure 4:
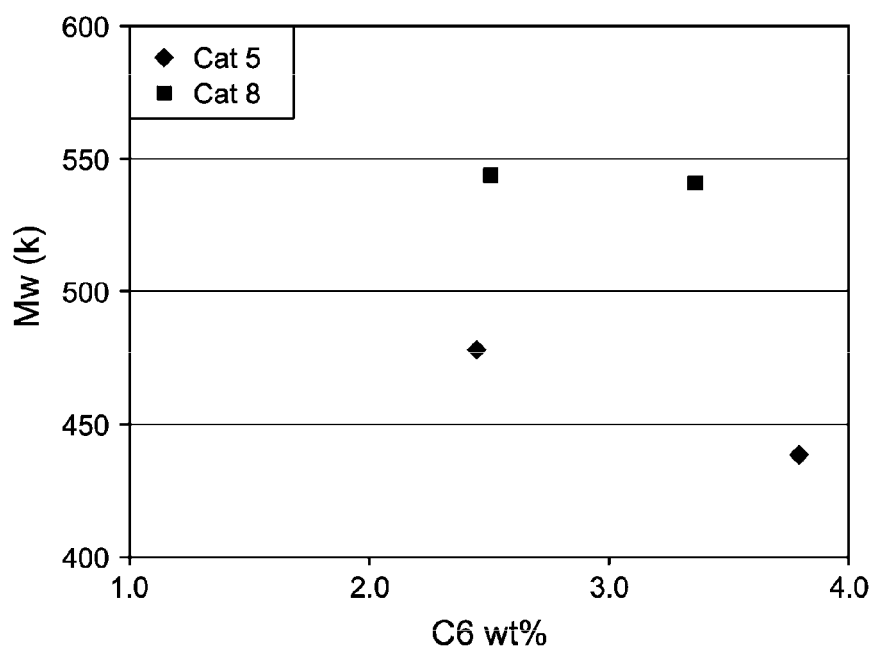
FIG. 4 is a Plot of Mw (k) vs C6 wt % for Catalyst 8 in comparison to Catalyst 5 in Table 2.
Figure 5:
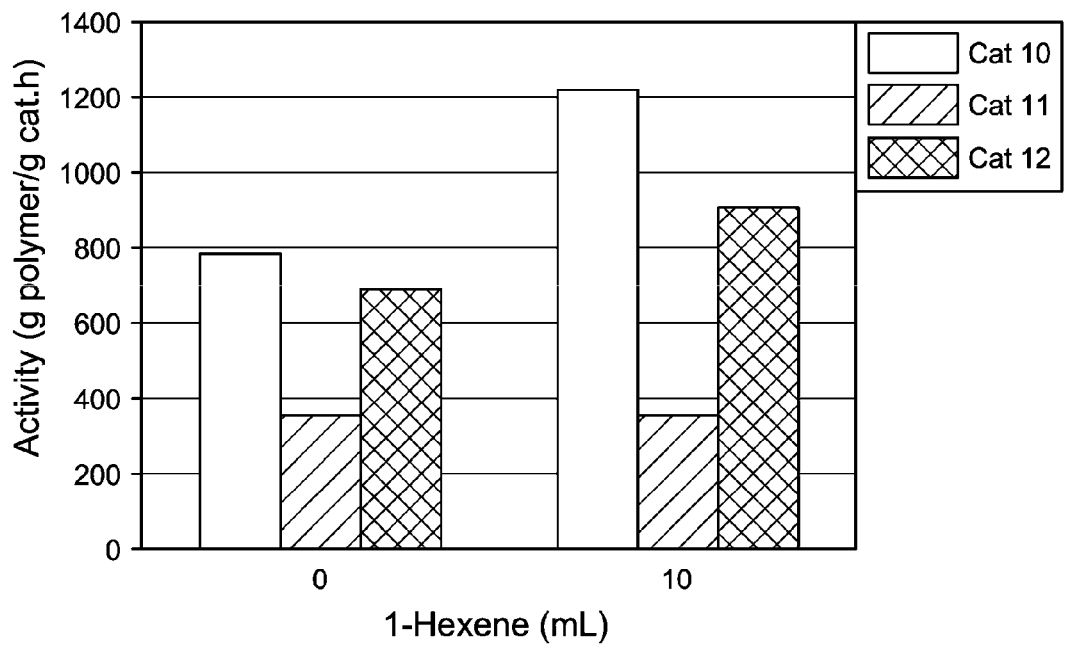
FIG. 5 is a comparison of activities of Catalysts 10, 11, and 12 from Table 3.

As shown in Table 2 and FIG. 3, Catalyst 8 and Catalyst 9 have higher Mw capabilities than other catalysts under similar 1-hexene feed conditions. As shown in FIG. 4, Catalyst 8 has higher Mw capabilities than another poor comonomer incorporating Catalyst 5 under similar C6 wt % incorporation conditions.

Figure 6:
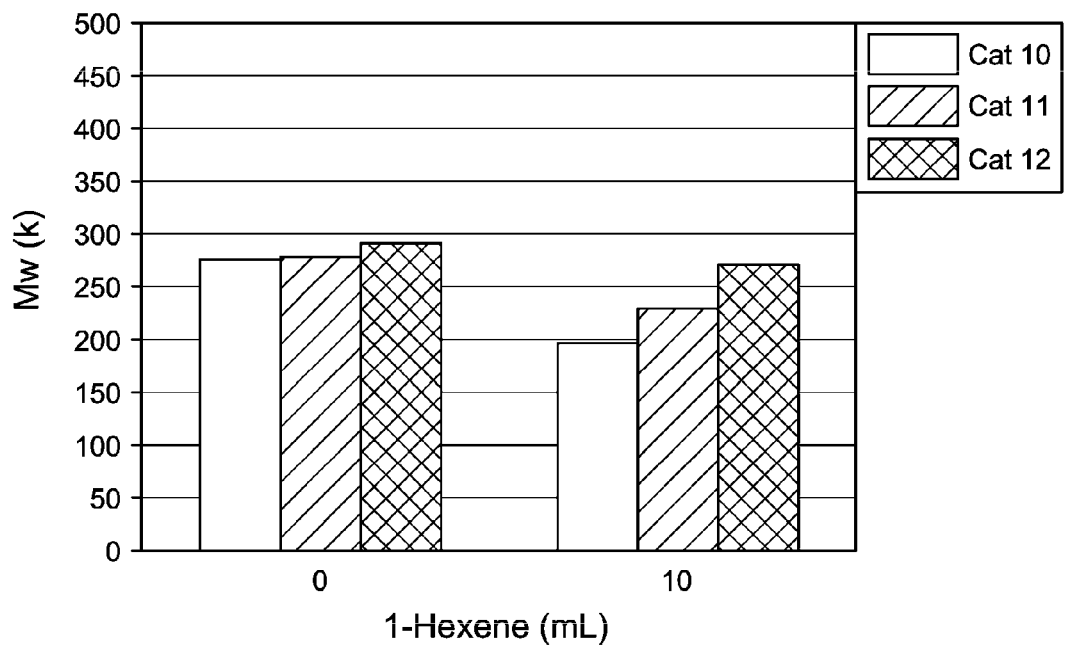
FIG. 6 is a comparison of molecular weights of polymers made by Catalysts 10, 11, and 12 from Table 3.

Surprisingly, as shown in Table 3, it appeared that rac-tetramethyldisilylene bis(4-(3',5'-di-tert-butylphenyl)-indenyl) zirconium dichloride and its meso isomer, when supported on Silica D948 using supporting procedure C, provided ethylene (co)polymers with similar Mw, MI and comonomer incorporation, with meso isomer (Catalyst 10) found to be more active and providing a broader PDI than rac isomer (Catalyst 11). Thus a 1/1 mixture of rac/meso isomers were co-supported on D948 using procedure C and this catalyst (Catalyst 12) provided ethylene (co)polymers with similar Mw, MI and broad MWD when compared with Catalyst 10 and Catalyst 11 (FIGS. 6 and 7).

Figure 7:
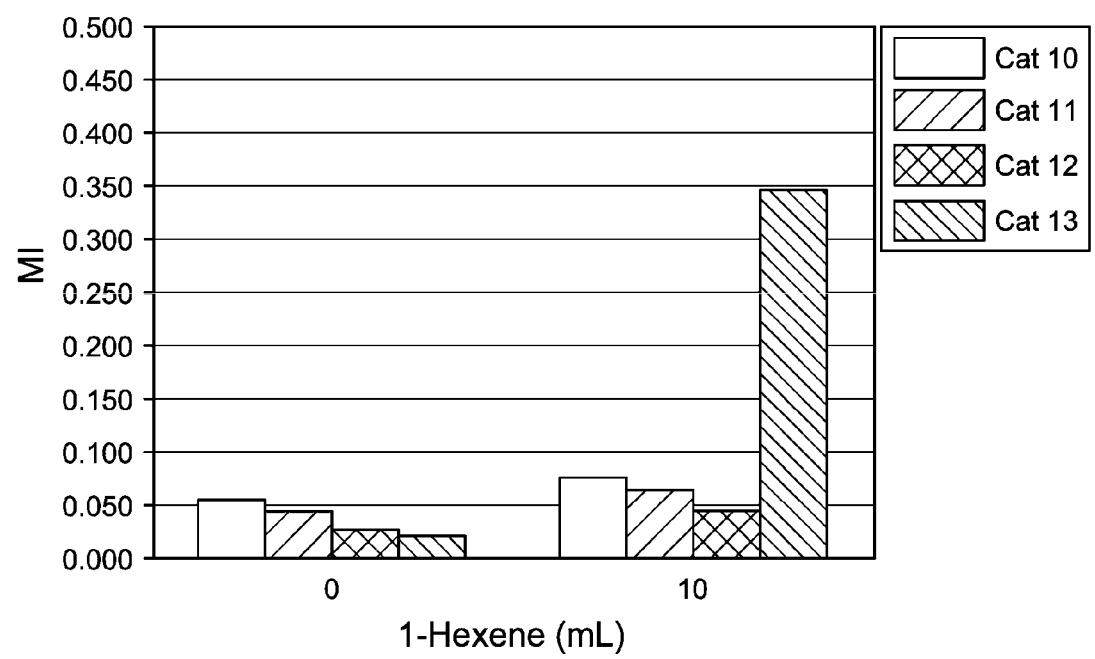
FIG. 7 is a representative plot of melt index (MI) vs. 1-hexene loadings for Catalyst 10, 11, 12, and Catalyst 13 from Table 3. Note MI of polymers made at 10 mL 1-hexene loading by Catalyst 13 are average of two runs shown in Table 3.
Figure 8B:
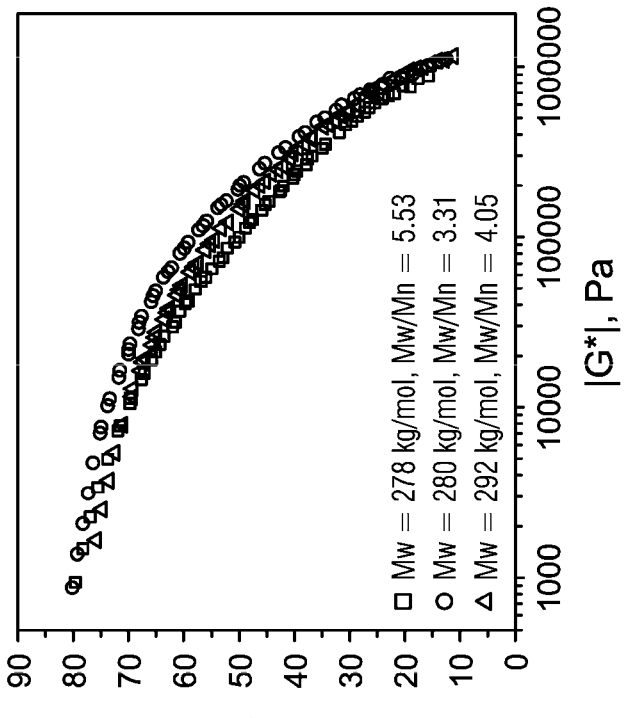
FIGS. 8A and 8B are plots of dynamic rheological measurements of polymers made by Catalysts 10, 11, and 12 (Runs 1, 3, and 5 from Table 3).
Figure 8A:
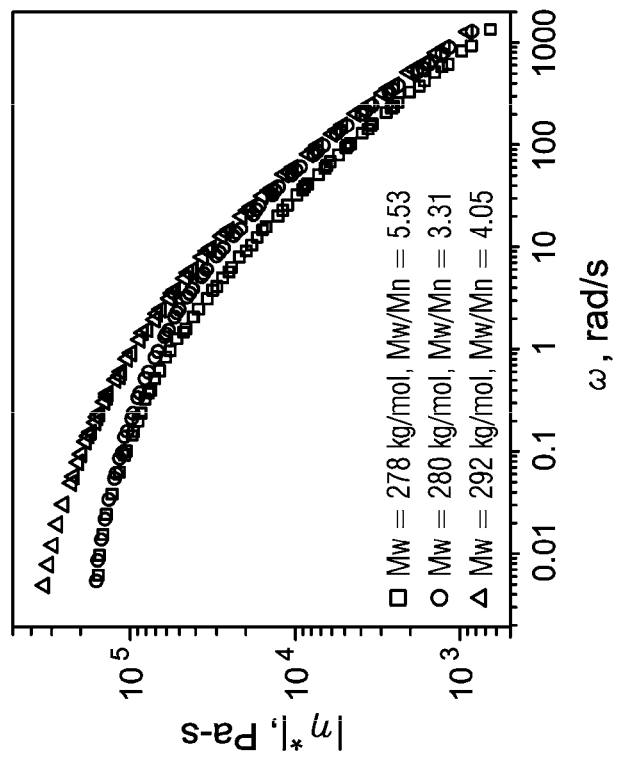
Figure 8D:
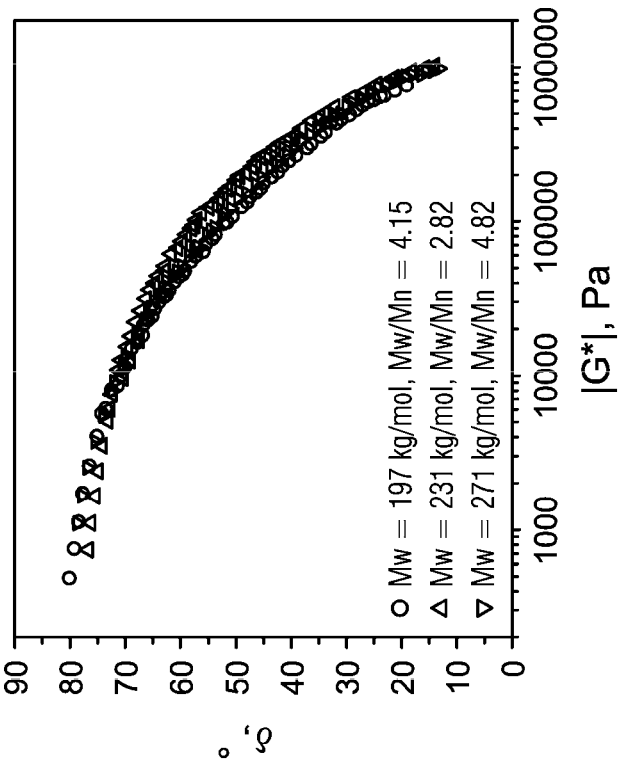
FIGS. 8C and 8D are plots of dynamic rheological measurements of polymers made by Catalysts 10, 11, and 12 (Runs 2, 4, and 6 from Table 3).
Figure 8C:
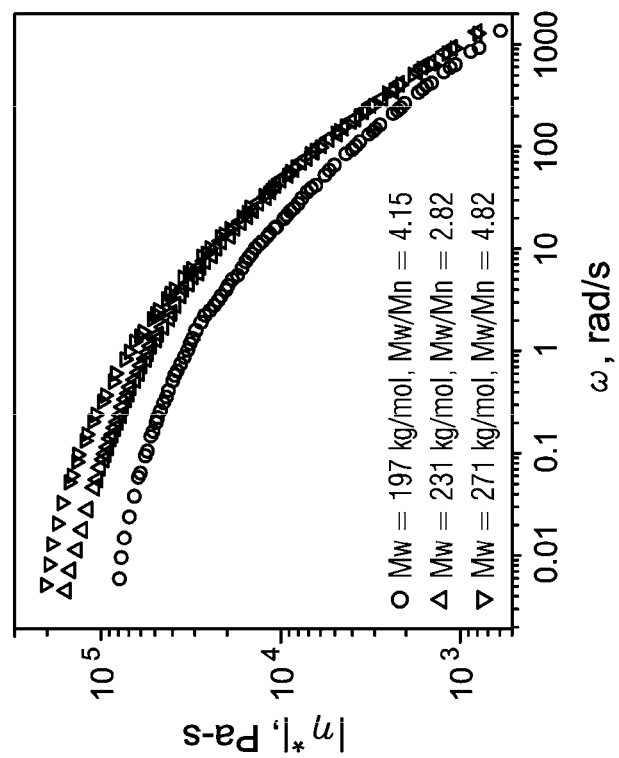
Figure 9A:
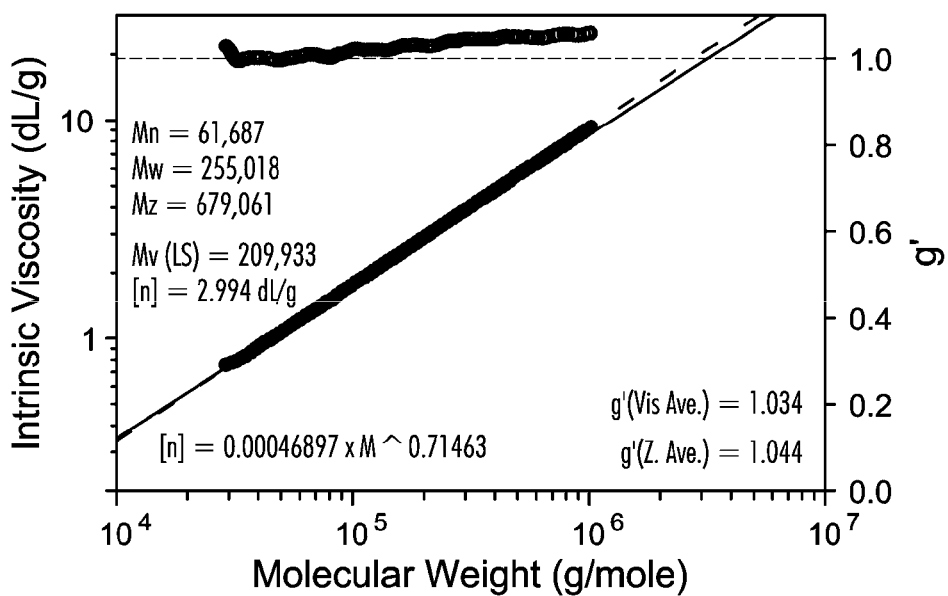
FIGS. 9A, 9B, 9C, and 9D are the GPC of polyethylene made by Catalyst 10 (Table 3, Run 1).
Figure 9B:
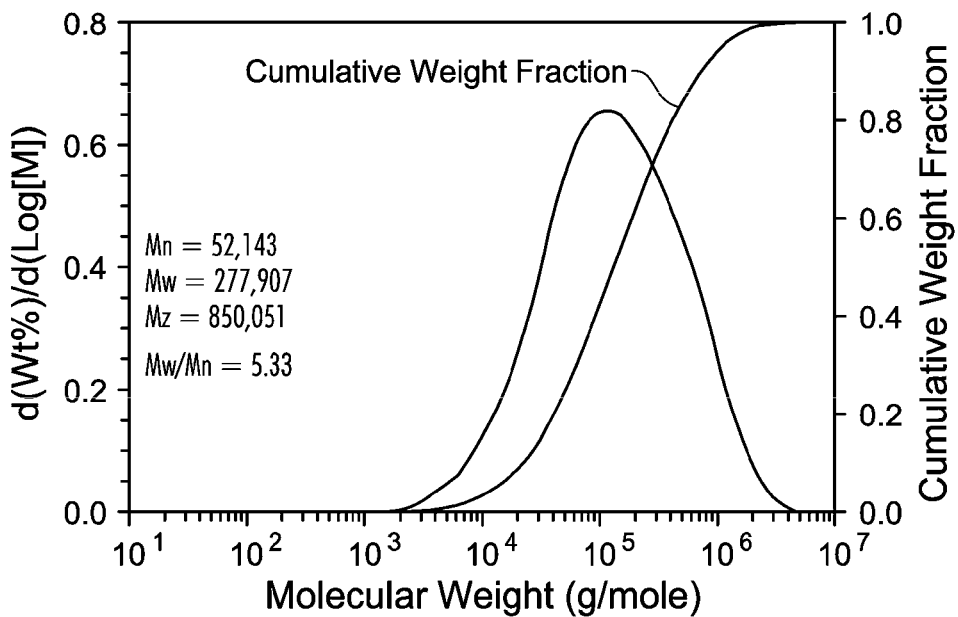
Figures 9C, 9D:
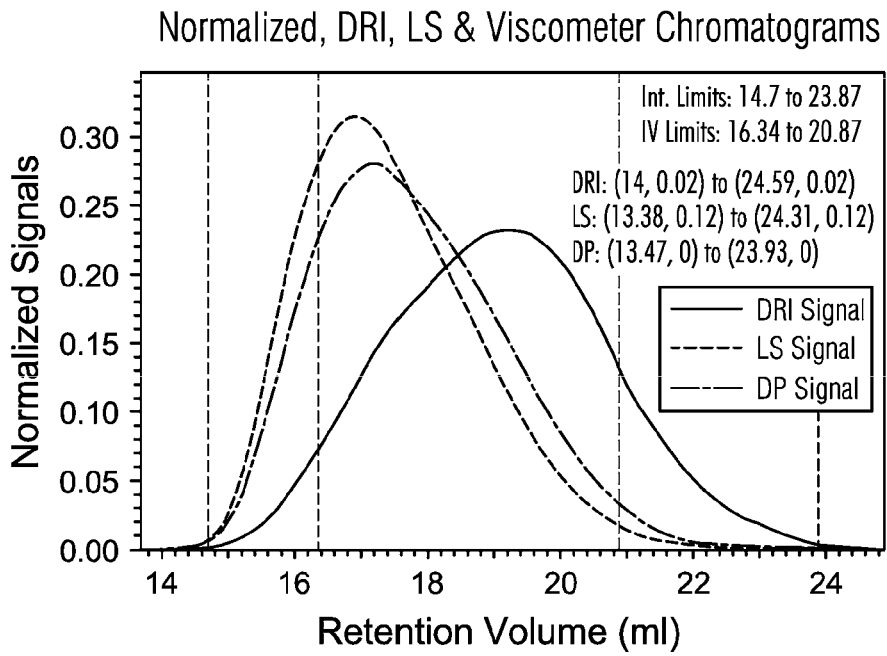
Figure 10A:
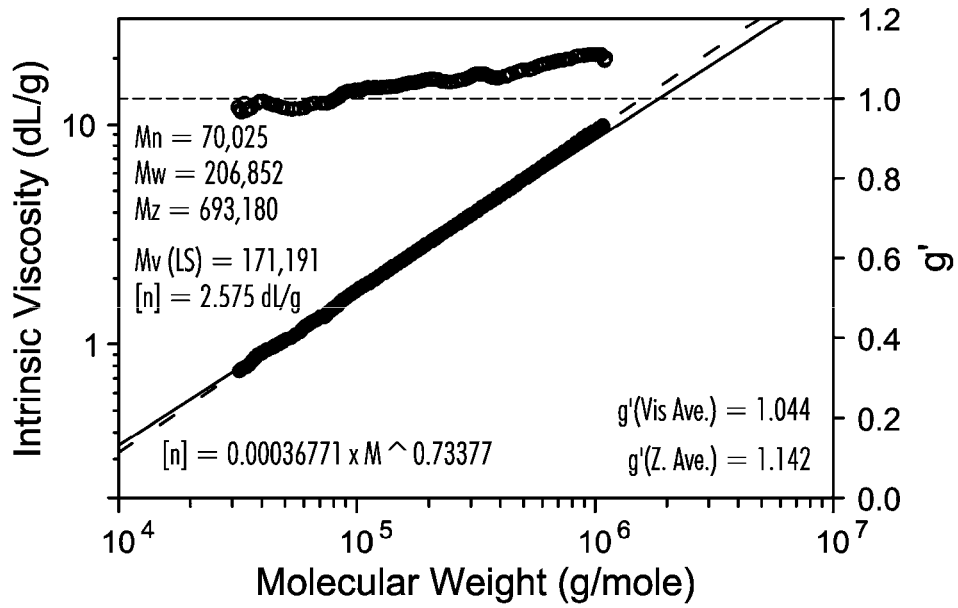
Figure 10B:
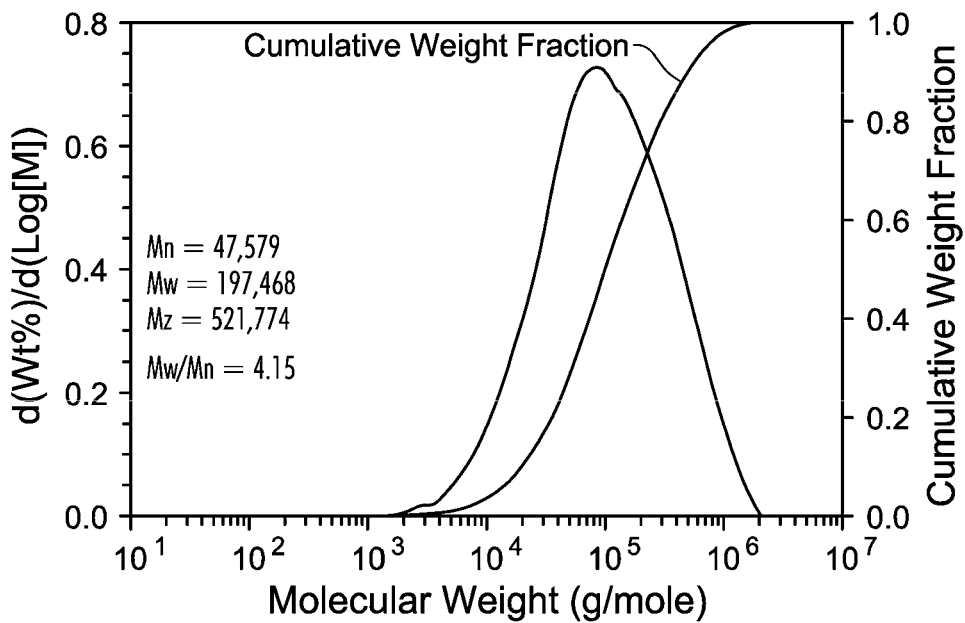

In addition, as illustrated in FIG. 7, when Catalyst 10 (meso-tetramethyldisilylene bis(4-(3',5'-di-tert-butylphenyl)-indenyl) ZrCl$_2$) was compared with Catalyst 13 (meso-Me$_4$Si$_2$-Ind$_2$ZrCl$_2$), in the presence of 1-hexene, Catalyst 10 provided EH copolymers with much lower MI (suggestive of higher Mw) than polymers made with Catalyst 13 under similar conditions. These data suggest Catalyst 10 (meso-isomer) with 2-H-4-3',5'-di-tert-butylphenyl substitutions on indene fragments has higher Mw capabilities in the presence of comonomer (e.g., 1-hexene) than Catalyst 13 (also meso-isomer) with simple indene fragments. It was noted that in addition to high Mw capabilities, Catalyst 10 has also shown very poor comonomer incorporation capabilities as well as good activities.

Rheological Measurements

Dynamic shear melt rheology was measured with a strain-controlled Rheometer ARES-G2 (TA Instruments) using parallel plates (diameter=25 mm) in dynamic mode. For all experiments, the temperature in the forced convection oven was maintained at 150° C. for at least 10 minutes before loading the compression molded samples into the parallel plates. Frequency sweeps in the range of 0.01 to 628 rad/s were carried out at six temperatures: 150° C., 170° C., 190° C., 210° C., 230° C., and 250° C., using strain amplitude of 10%. A stream of nitrogen is circulated in the oven to hinder degradation or crosslinking of the samples during the experiments. Dynamic master curves of the elastic and viscous modulus (G' and G", respectively) were constructed using the time-temperature superposition (tTs) principle, that is by horizontally shifting the curves of G' and G" vs. frequency ($\omega$), until all the curves overlap. The data at 190° C. was used as reference for the shifting. The complex viscosity ($|\eta^*|$), the phase angle ($\delta$) and the complex modulus ($|G^*|$) are computed from the master curve data of G', G" and $\omega$, as $$\delta = G''/G'$$

$$|G^*| = (G'^2 + G''^2)^{0.5}$$

$$|\eta^*| = |G^*|/\omega.$$

As shown from FIGS. 8A, 8B, 8C, and 8D, the linear viscoelastic responses of the six samples show behavior for linear polymers: single monotonic relaxation mode, evidencing absence of long chain branches.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A catalyst compound represented by the formula:

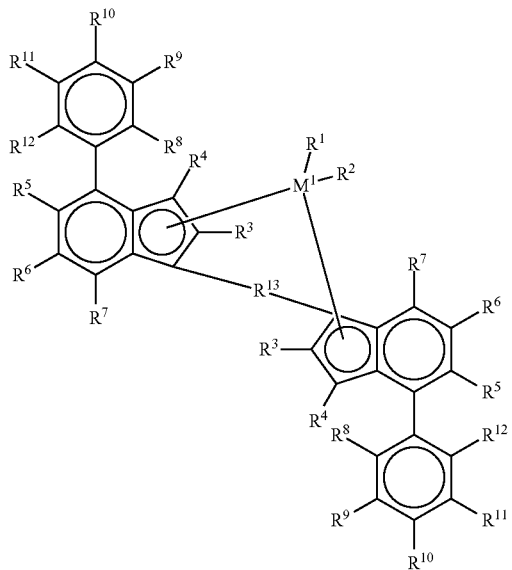

(I)

wherein $M^1$ is selected from the group consisting of titanium, zirconium, and hafnium;

each $R^1$ and $R^2$ are identical or different and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri (hydrocarbyl) silyl groups or tri (hydrocarbyl) silylhydrocarbyl groups, said diene having up to 30 atoms not counting hydrogen;

each $R^4$ to $R^7$ are identical or different and are each a hydrogen atom, or a substituted or unsubstituted, branched or unbranched $C_1$-$C_{10}$ alkyl group;

each $R^3$ are identical or different and are each a hydrogen atom, or a substituted or unsubstituted, branched or unbranched $C_2$-$C_{10}$ alkyl group;

$R^{13}$ is —$((R^{15*})_2Si-Si(R^{15})_2)$— wherein, each $R^{15}$ and $R^{15*}$ is identical or different and is a substituted or unsubstituted, branched or unbranched $C_1$-$C_{20}$ alkyl group;

each $R^8$, $R^{10}$ and $R^{12}$ are identical or different and are each a hydrogen atom or a substituted or unsubstituted, branched or unbranched $C_1$-$C_{10}$ alkyl group; and each $R^9$ and $R^{11}$ are identical or different and are a hydrogen atom or a substituted or unsubstituted, branched or unbranched $C_2$-$C_{20}$ alkyl group.

2. The catalyst compound of claim 1, wherein $M^1$ is Hf or Zr.

3. The catalyst compound of claim 1, wherein each $R^3$ is a hydrogen atom and $R^8$ through $R^{12}$ are each hydrogen atoms.

4. The catalyst compound of claim 1, wherein each $R^3$ is a hydrogen atom or a $C_2$-$C_{10}$ alkyl group, $R^8$, $R^{10}$ and $R^{12}$ are each hydrogen atoms and each $R^9$ and $R^{11}$ are identical or different and are each a $C_3$-$C_{20}$ alkyl group.

5. The catalyst compound of claim 4, wherein each $R^3$ is a hydrogen atom and each $R^9$ and $R^{11}$ are each t-butyl groups.

6. The catalyst compound of claim 1, wherein the catalyst compound has a rac/meso ratio is from 100/1 to 1/100.

7. A supported catalyst composition comprising a support and the catalyst compound of claim 1.

8. The supported catalyst composition of claim 7, wherein the support is fluorided silica.

9. A catalyst system comprising activator and the catalyst compound of claim 1.

10. A process to polymerize ethylene comprising contacting ethylene and, optionally, one or more olefin comonomers, with the catalyst system of claim 9; wherein the polymer produced has at least 50 mol% ethylene and an $M_w$ between 20,000 g/mol and 400,000 g/mol.

11. The process of claim 10, wherein the rac and meso forms of the catalyst compound are not separated.

12. The process of claim 10, wherein the comonomers comprise one or more of propylene, butene, pentene, hexene, heptene, octene, nonene, decene, undecene, dodecene and isomers thereof.

13. The process of claim 10, wherein the polymer has a PDI greater than 4, and has a g'vis of 0.95 or more.

14. The process of claim 10, wherein the process occurs at a temperature of from about 0° C. to about 300° C., at a pressure in the range of from about 0.35 MPa to about 10 MPa, and at a time up to 300 minutes.

15. The process of claim 10, wherein the activator comprises alumoxane.

16. The process of claim 10, wherein the activator comprises a non-coordinating anion activator.

17. The process of claim 10, wherein the polymer comprises less than 15% comonomer, based upon the weight of the polymer, and the polymer has an $M_w$ of 190,000 g/mol or more.

18. The process of claim 13, wherein the meso form of the catalyst or meso/rac mixtures of the catalyst provide a polymer with a Mw/Mn greater than 4.

19. The process of claim 13, wherein the rac form of the catalyst provides a polymer with a Mw/Mn of 2 to 3.

20. The catalyst compound of claim 1, wherein each $R^{15}$ together do not form a ring, and each $R^{15*}$ together do not form a ring.

21. The catalyst compound of claim 1, wherein $R^{15}$ and $R^{15*}$ together do not form a ring.

22. The catalyst compound of claim 1, wherein each $R^{15}$ together do not form a ring, and each $R^{15*}$ together do not form a ring, and $R^{15}$ and $R^{15*}$ together do not form a ring.

23. A catalyst system comprising activator and the catalyst compound of claim 1, wherein each $R^{15}$ together do not form a ring, and/or each $R^{15*}$ together do not form a ring, and/or $R^{15}$ and $R^{15*}$ together do not form a ring.

24. A process to polymerize ethylene comprising contacting ethylene and, optionally, one or more olefin comonomers, with the catalyst system of claim 23; wherein the polymer produced has at least 50 mol % ethylene and an $M_w$ between 20,000 g/mol and 400,000 g/mol.

25. A catalyst compound represented by the formula:

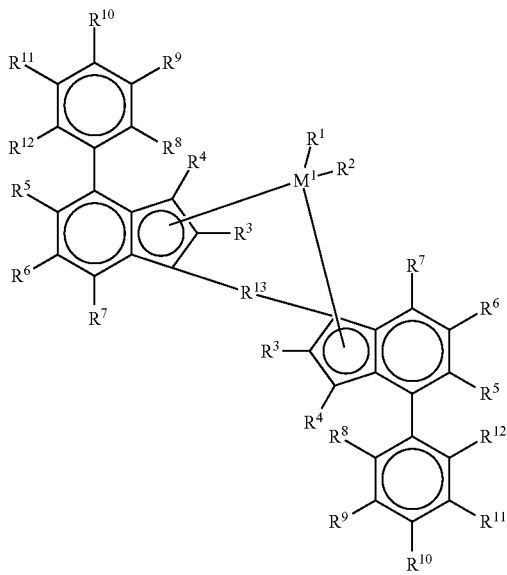

(I)

wherein $M^1$ is selected from the group consisting of titanium, zirconium, and hafnium;

each $R^1$ and $R^2$ are identical or different and are each a hydrogen atom, a $C_1$-$C_{10}$ alkyl group, a $C_1$-$C_{10}$ alkoxy group, a $C_6$-$C_{10}$ aryl group, a $C_6$-$C_{10}$ aryloxy group, a $C_2$-$C_{10}$ alkenyl group, a $C_2$-$C_{40}$ alkenyl group, a $C_7$-$C_{40}$ arylalkyl group, a $C_7$-$C_{40}$ alkylaryl group, a $C_8$-$C_{40}$ arylalkenyl group, an OH group or a halogen atom, or a conjugated diene which is optionally substituted with one or more hydrocarbyl, tri (hydrocarbyl) silyl groups or tri (hydrocarbyl) silylhydrocarbyl groups, said diene having up to 30 atoms not counting hydrogen;

each $R^4$ to $R^7$ are identical or different and are each a hydrogen atom, or a substituted or unsubstituted, branched or unbranched $C_1$-$C_{10}$ alkyl group;

each $R^3$ are different and are each a hydrogen atom, or a substituted or unsubstituted, branched or unbranched $C_1$-$C_{10}$ alkyl group;

$R^{13}$ is —$((R^{15*})_2Si—Si(R^{15})_2)$— wherein, each $R^{15}$ and $R^{15*}$ is identical or different and is a substituted or unsubstituted, branched or unbranched $C_1$-$C_{20}$ alkyl group;

each $R^8$, $R^{10}$ and $R^{12}$ are identical or different and are each a hydrogen atom or a substituted or unsubstituted, branched or unbranched $C_1$-$C_{10}$ alkyl group; and each $R^9$ and $R^{11}$ are identical or different and are a hydrogen atom or a substituted or unsubstituted, branched or unbranched $C_2$-$C_{20}$ alkyl group.

26. The catalyst compound of claim 1, wherein $R^3$ are identical and are each a hydrogen atom.

27. A supported catalyst composition comprising a support and the catalyst compound of claim 26.

28. The supported catalyst composition of claim 27, wherein the support is fluorided silica.

29. A catalyst system comprising activator and the catalyst compound of claim 26.

30. A process to polymerize ethylene comprising contacting ethylene and, optionally, one or more olefin comonomers, with the catalyst system of claim 29, wherein the polymer produced has at least 50 mol% ethylene and an $M_w$ between 20,000 g/mol and 400,000 g/mol.

31. The process of claim 30 wherein the activity of the catalyst is 5000 g/mmol/hr or more.

32. The process of claim 10 wherein the activity of the catalyst is 5000 g/mmol/hr or more.

33. The catalyst compound of claim 26, wherein each $R^9$ and $R^{11}$ are identical or different and are each a $C_3$-$C_{20}$ alkyl group.

34. The catalyst compound of claim 26, wherein each $R^9$ and $R^{11}$ are identical or different and selected from butyl, pentyl, hexyl, heptyl, octyl, nonyl, decyl, undecyl, dodecyl and isomers thereof, which may be halogenated, and $C_6$-$C_{10}$ aryl groups which may be halogenated.

35. The process of claim 30 wherein the activator comprises a non-coordinating anion activator.

36. The process of claim 30 wherein two or more different catalyst compounds are present in the catalyst system.

* * * * *